United States Patent
Kumar et al.

(10) Patent No.: US 7,456,147 B2
(45) Date of Patent: *Nov. 25, 2008

(54) CONTROLLED RELEASE OF ACTIVE AGENTS UTILIZING REPEAT SEQUENCE PROTEIN POLYMERS

(75) Inventors: Manoj Kumar, Fremont, CA (US); Isabelle Mazeaud, Chatellerault (FR); Steven Patrick Christiano, Midland, MI (US)

(73) Assignees: Dow Corning, Corporation, Midland, MI (US); Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/845,775

(22) Filed: May 14, 2004

(65) Prior Publication Data

US 2004/0228913 A1 Nov. 18, 2004

Related U.S. Application Data

(60) Provisional application No. 60/470,465, filed on May 14, 2003.

(51) Int. Cl.
*A61K 38/00* (2006.01)
*C07K 2/00* (2006.01)

(52) U.S. Cl. .......................................... 514/2; 530/300
(58) Field of Classification Search ................. 424/468; 530/350
See application file for complete search history.

(56) References Cited

U.S. PATENT DOCUMENTS

| | | | |
|---|---|---|---|
| 5,243,038 A | 9/1993 | Ferrari et al. | |
| 5,412,074 A | 5/1995 | Jones et al. | |
| 5,433,953 A * | 7/1995 | Tsuei et al. | ................. 424/489 |
| 5,626,853 A | 5/1997 | Bara et al. | |
| 5,627,148 A | 5/1997 | Dubief et al. | |
| 5,679,543 A | 10/1997 | Lawlis | |
| 6,004,444 A | 12/1999 | Aksay et al. | |
| 6,034,220 A | 3/2000 | Stedronsky | |
| 6,153,602 A | 11/2000 | Dubief et al. | |
| 6,184,348 B1 | 2/2001 | Ferrari et al. | |
| 6,228,248 B1 | 5/2001 | Aksay et al. | |
| 6,355,776 B1 | 3/2002 | Ferrari et al. | |
| 6,358,501 B1 | 3/2002 | Dietz et al. | |
| 6,365,661 B1 | 4/2002 | Fischer et al. | |
| 6,365,877 B1 | 4/2002 | Chen et al. | |
| 6,368,606 B1 | 4/2002 | Dubief et al. | |
| 2001/0006664 A1 | 7/2001 | Ensley | |
| 2001/0013294 A1 | 8/2001 | Bruno et al. | |
| 2001/0027570 A1 | 10/2001 | Blees | |
| 2002/0064539 A1 | 5/2002 | Philippe et al. | |
| 2005/0142094 A1 * | 6/2005 | Kumar | ..................... 424/70.14 |

FOREIGN PATENT DOCUMENTS

| | | |
|---|---|---|
| EP | 0 540 357 A2 | 5/1993 |
| EP | 0 699 431 A1 | 3/1996 |
| WO | WO 00/35993 | 6/2000 |
| WO | WO 01/46213 A2 | 6/2001 |
| WO | WO 01/87825 A1 | 11/2001 |

OTHER PUBLICATIONS

Cappello, J. et al. Journal of Controlled Release 53: 105-117 (1998).*
Fischel-Ghodsian, F. et al. Proc. Natl. Acad. Sci. 85: 2403-2406 (1988).*
Nagarsekar, A. et al. J Biomed Mater Res 62: 195-203 (2002).*
Megeed, Z. et al. Pharmaceutical Research 19(7): 954-959 (2002).*
Haider et al., "Genetically engineered polymers: status and prospects for controlled release", Journal of Controlled Release 95: 1-26 (2004).*
Deming, Facile synthesis of block copolypeptides of defined architecture, Nature, vol. 390, Nov. 27, 1997, pp. 386-389.
Fan, et al., Rapid prototyping of patterned functional nanostructures, Nature, vol. 405, May 4, 2000, pp. 56-60.
Brott et al., Ultrafast holographic nanopatterning of biocatalytically formed silica, Nature, vol. 413, Sep. 20, 2001, pp. 291-293.
Huo et al., Generalized synthesis of periodic surfactant/inorganic composite materials, Nature, vol. 368, Mar. 24, 1994, pp. 317-321.
Zhou et al., Efficient Catalysis of Polysiloxane Synthesis by Silicatein Requires Specific Hodroxy and Imidazole Functionalities, Angew. Chem. Inst., Ed. 1999, 38, No. 6, pp. 779-782.
Gosline et al., Elastic proteins: biological roles and mechanical properties, The Royal Society, Feb. 28, 2002, pp. 121-132.
Kroger et al., Polycationic Peptides from Diatom Biosilica That Direct Silica Nanosphere Formation, Science, vol. 286, Nov. 5, 1999, pp. 1129-1132.
Naik et al., Silica-Precipitating Peptides Isolated from a Combinatorial Phage Display Peptide Library, Journal of Nanoscience and Nanotechnology, 2002, vol. 2, No. 1, pp. 95-100.
Kroger et al., Silica-precipitating Peptides from Diatoms, The Chemical Structure of Silaffin-1A From Cylindrotheca Fusiformis, J. Biol. Chem., vol. 276, Issue 28, 26066-26070, Jul. 13, 2001, pp. 1-12.
Mizutani et al., Silicic Acid Polymerization Catalyzed by Amines and Polyamines, Bull. Chem. Soc. Jpn., 71, 2017-2022 (1998).
Mizutani et al., Silicic Acid Polymerization Catalyzed by Amines and Polyamines, Chemistry Letters, 1998 pp. 133-134.
Hartgerink et al., Peptide-amphiphile nanofibers: A versitile scaffold for the preparation of self-assembling materials, PNAS, Apr. 16, 2002, vol. 99, No. 8 pp. 5133-5138.
Zhang, Emerging biological materials through molecular self-assembly, Elsevier, Biotechnology Advances 20 (2002) pp. 321-339.
Wong et al., Assembly of Nanoparticles into Hollow Spheres Using Block Copolypeptides, Nano Letters, vol. 2, No. 6, pp. 583-587, 2002.

(Continued)

*Primary Examiner*—Anand U Desai
(74) *Attorney, Agent, or Firm*—Dinsmore & Shohl LLP

(57) ABSTRACT

Systems are provided for the controlled release delivery of active agents through the use of repeat sequence protein polymers. The systems may exist as matrices, gels, hydrogels, films, emulsions or microparticles and are particularly useful for incorporating active agents into personal care product compositions.

31 Claims, No Drawings

OTHER PUBLICATIONS

Naik et al., Silica-Precipitating Peptides Isolated from a Combinatorial Phage Display Peptide Library, Journal of Nanoscience and Nanotechnology, 2002, vol. 2, No. 1, pp. 95-100.

Arkles, Commercial Applications of Sol-Gel-Derived Hybrid Materials, Mrs. Bulletin, May 2001, pp. 402-408.

Sarikaya, Biometrics: Materials fabrication through biology, PNAS, Dec. 7, 1999. vol. 96, No. 25, pp. 14183-14185.

Alvarez, Engineering Protein Molecules for the Ordered Structuring of Silica, National Nanofabrication Users Network, pp. 82-83.

Coradin et al., Biogenic Silica Patterning: Simple Chemistry or Subtle Biology? ChemBioChem 2003, 3, pp. 1-9.

* cited by examiner

US 7,456,147 B2

CONTROLLED RELEASE OF ACTIVE AGENTS UTILIZING REPEAT SEQUENCE PROTEIN POLYMERS

RELATED APPLICATION

This application claims priority under 35 U.S.C. §119 of U.S. Provisional Application Ser. No. 60/470,465, filed May 14, 2003.

STATEMENT OF JOINT RESEARCH AGREEMENT

The present invention, as defined by the claims herein, was made by parties to a Joint Research Agreement between Genencor International, Inc. and The Dow Corning Corporation.

FIELD OF THE INVENTION

The present invention relates to a system for providing the controlled release delivery of an active agent, and, more particularly, to a system utilizing repeat sequence protein polymers to provide controlled release of active agents. In one aspect, the invention relates to personal care compositions utilizing repeat sequence protein polymers to provide controlled release of active agents.

BACKGROUND OF THE INVENTION

Many active agents such as proteins, enzymes and vitamins have been used in personal care products to impart desired characteristics to the product. It is sometimes desirable for active agents to be delivered to hair, skin, nails, and teeth in a controlled manner. Additionally, it is sometimes desirable for active agents such as enzymes to remain in an active form in personal care products. However, many components of personal care products may inactivate active agents. Proteins may be chemically modified or quaternized in order to make them more suitable for inclusion in personal care products. However, even chemically modified proteins may not have all desired characteristics. Thus, there remains a need in the art for proteins that have desired characteristics and for proteins that may be included in personal care formulations without chemical modification. There is also a need in the art for improving the ease of formulation of these proteins into personal care products and in delivery to the skin or hair. Additionally there remains a need in the art for methods and formulations for providing controlled release of active agents in personal care products.

SUMMARY OF THE INVENTION

Accordingly, the present invention relates to systems that provide controlled release of active agents by utilizing repeat sequence protein polymers. Repeat sequence protein polymers may be used to form complexes, and the complexes may be further processed to provide the systems, for example, matrixes, emulsions, gels, films, and microparticles. In specific embodiments, recombinant engineered forms of the repeat sequence protein polymers are employed. The repeat sequence protein polymers generally comprise naturally occurring repeat sequences such as those found in silk or elastin. The repeat sequence protein polymers may provide controlled release properties, with specific embodiments providing triggered controlled release of an active agent.

Other embodiments are directed to personal care product compositions comprising the systems providing controlled release, with further embodiments directed to processes for making such personal care product compositions. The processes comprise combining a system for providing controlled release delivery of an active agent with a physiologically acceptable carrier or excipient to obtain a personal care composition.

Alternatively, repeat sequence protein polymers, including recombinant forms, may be used in conjunction with at least one active agent to form microparticles by interfacial polymerization, and a complex is generally not formed.

In accordance with another aspect of this invention, methods are provided which enhance the delivery of repeat sequence protein polymers into personal care compositions. These methods comprise forming highly stable silicone-repeat sequence protein polymer complexes and adding the complexes to personal care compositions. A further embodiment is directed to the silicone-repeat sequence protein polymer complexes wherein at least one repeat-sequence protein polymer comprises a genetically engineered silk-elastin like protein. More specific embodiments of the present invention provide silicone emulsions comprising the complexes which provide particular benefits when employed in personal care composition products.

DETAILED DESCRIPTION OF THE PREFERRED EMBODIMENTS

Embodiments of the present invention utilize recombinant repeat protein sequence polymers containing repeating units to provide, for example, controlled release of active agents for personal care products.

For purposes of defining and describing the present invention, "repeat sequence protein polymer"0 (RSPP) refers to a polymer comprising repeating amino acid sequence units, which repeating units are derived from a natural or synthetic protein. For example, the repeating sequence units may be derived from natural structure supporting materials such as silk, elastin, and collagen. Alternatively, the repeating sequence units may be derived from synthetic structures.

For purposes of defining and describing the present invention, "personal care composition" refers to a product for application to the skin, hair, nails, oral cavity and related membranes for the purposes of improving, cleaning, beautifying, therapeutically treating, caring for these surfaces and membranes.

For purposes of defining and describing the present invention, "an effective amount" refers to the amount of repeat sequence protein polymer which is added to a personal care composition to provide the composition with a desired characteristic or characteristics.

For purposes of defining and describing the technology, the term "dispersed phase" is a term well-known to one skilled in the art of emulsion technology, which means that the phase exists as small particles or droplets that are suspended in and surrounded by a continuous phase. The dispersed phase is also known as the internal or discontinuous phase.

For purposes of defining and describing the present invention "active agent" shall be understood as referring to a suitable product component including, but not limited to, silicones, fragrances, dyes, tints, UV actives, sunscreens, lanolin, vitamins, bleaches, thickening agents, proteins, peptides, enzymes, antimicrobials and preservatives.

For purposes of defining and describing the present invention, the term "protein" as used herein, shall be understood as comprising greater than fifty (50) amino acids, while the term "peptide" as used herein, shall be understood as comprising 50 or less amino acids.

In general, the repeat sequence protein polymers may be used in a variety of manners to provide controlled release of active agents. For example, the repeat sequence protein polymer may be used to form complexes with active agents, to act as a rate controlling polymer, and to serve as a component to microencapsulate active agents.

The repeating units of the repeat sequence protein polymers of the present invention may be derived from natural structure supporting materials such as silk, elastin, and collagen. Alternatively, the repeating units may be derived from synthetic structures. Typically, the repeat sequence protein polymers are synthesized and added to hair conditioning or other hair product formulations, skin products, oral care products, or nail products, and the like.

The recombinant repeat sequence protein polymers are comprised of naturally or non-naturally occurring repeating units. There are more than six hundred repeat protein sequences known to exist in biological systems as of the filing of this application. Utilizing repeat sequence protein polymers may provide increased conditioning, nourishment, and repair properties to hair care formulations. For example, well known proteins containing repeat protein sequences include abductin, elastin, byssus, flagelliform silk, dragline silk, gluten high molecular weight (HMW) subunit, titin, fibronectin, leminin, and collagen. Additionally, synthetic repeating units may be utilized. Individual repeating units will generally comprise from 3 to 30 amino acids, and will usually have the same amino acid appearing at least twice in the same unit. Typically, individual units will comprise from about 3 to 8 amino acids. Therefore, each individual unit will typically be formed from about 3 to 8 amino acids. Different unit combinations may be joined together to form a block copolymer or alternating block copolymer. Typically, the copolymers will have the following formula:

$$T_y[(A_n)_x(B)_b(A'_{n'})_{x'}(B')_b(A''_{n''})_{x''}]_iT_{y'}$$

wherein:

T is an amino acid sequence of from about 1 to 100 amino acids, usually 1 to 60 amino acids, which may be any sequence, generally being fewer than 20% of the total number of amino acids in the repeat protein copolymer;

y is 0 or 1;

T' and y' are the same as or different from T and y respectively, wherein the analogous symbols have the same definition as their counterparts;

A is an individual unit of a repeat amino acid sequence;

n is an integer of at least 2 and not more than 250;

x is 0 or an integer of at least 1 and will vary with the number of different amino acids in A so as to provide for at least 30 amino acids in each A repeat sequence;

A', n', and x' are the same as or different from A, n, and x respectively, at least one being different, wherein the analogous symbols have the same definition as their counterparts;

A", n", and x" are the same as or different from A, n, and x respectively, at least one being different, wherein the analogous symbols have the same definition as their counterparts;

B is any amino acid sequence of 4 to 50 amino acids, usually being a functional sequence that results in a biological or chemical function or activity;

b is 0 to 3;

B' and b' are the same as or different from B and b respectively, wherein the analogous symbols have the same definition as their counterparts; and i is 1 to 100, usually 1 to 50, more usually 1 to 30.

Additionally, the protein polymer may have amino acid sequences that link the repeating A, A', and A" units or amino acid sequences that link between the individual A, A' or A" units. These linking sequences are typically from 1 to 10 amino acids and serve to link the repeating units. These repeat polymers can be synthesized by generally recognized methods of chemical synthesis (For example, L. Andersson et. al., *Large-scale synthesis of peptides*, Biopolymers 55(3), 227-50 (2000)), genetic manipulation (For example, J. Cappello, Genetically Engineered Protein Polymers, Handbook of Biodegradable Polymers, Domb, A. J.; Kost, J.; Wiseman, D. (Eds.), Harvard Academic Publishers, Amsterdam; pages 387-414), and enzymatic synthesis (For example, C. H. Wong & K. T. Wang, *New Developments in Enzymatic Peptide Synthesis*, Experientia 47(11-12), 1123-9 (1991)). For example, the repeat sequence protein polymers of the present invention may be synthesized using the methods described in U.S. Pat. Nos. 5,243,038 and 6,355,776, the disclosures of which are incorporated by reference herein. In another example, the repeat sequence protein polymers can by synthesized utilizing non-ribosomal peptide synthase (for example, H. V. Dohren, et al., Multifunctional Peptide Synthase, Chem.Rev 97, 2675-2705(1997). The repeat sequence protein polymers may be produced on a commercial scale.

Individual repeat amino acid sequence units of particular interest include units found in silk-, elastin-, collagen-, abductin-, byssus-, gluten-, titin-, extensin-, and fibronectin-like proteins. Silk-like proteins have a repeating unit of SGAGAG (G=glycine; A=alanine; S=serine) (SEQ ID NO. 1). This repeating unit is found in naturally occurring silk fibroin protein, which can be represented as GAGAG (SGAGAG)$_8$SGAAGY (Y=tyrosine) (SEQ ID NO. 2). Elastin-like proteins have a base repeating unit of GVGVP (V=valine; P=proline) (SEQ ID NO.3). This repeating unit may be found in naturally occurring elastin. Collagen-like proteins have repeating units of G-x-y (x=any amino acid, often alanine or proline; y=any amino acid, often proline or hydroxy-proline). Abductin-like proteins have a base repeating unit of GGFGGMGGGx (F=phenylalanine; M=methionine, x=any amino acid) (SEQ ID NO. 4). Byssus-like proteins have a repeating unit of (GPGGG) (SEQ ID NO. 5). Gluten-like proteins of the high molecular weight subunit have repeating units of PGQGQQ (SEQ ID NO. 6), GYYPTSPQQ (SEQ ID NO. 7), and GQQ (Q=glutamine; Y=tyrosine; T=threonine) SEQ ID NO. 8). Titin-like proteins have repeating units of PPAKVPEVPKKPVPEEKVPVPVP-KKPEA (K=Lysine, E=Glutamic Acid) (SEQ ID NO. 9) and are found in the heart, psoas, and soleus muscle. Extensin-like proteins have repeating units of SPPPPSPKYVYK (SEQ ID NO. 10). Fibronectin-like proteins have repeating units of RGDS (R=arginine; D=aspartic acid) (SEQ ID NO. 11).

Additional repeating units of interest are found in gliadin, glue polypolypeptide, ice nucleating protein, keratin, mucin, RNA polymerase II, and resilin. Gliadin has a repeating unit of PQQPY (SEQ ID NO. 12). The glue polypeptide has a repeating unit of PTTTK (SEQ ID NO. 13). The ice nucleating protein has a repeating unit of AGYGSTGT (SEQ ID NO. 14). Keratin has repeating units of YGGSSGGG (SEQ ID NO. 15) or FGGGS (SEQ ID NO. 16). Mucin has a repeating unit of TTTPDV (Seq. ID No. 17). RNA polymerase II has a repeating unit of YSPTSPS (SEQ ID NO. 18). Additionally, resilin, a rubber-like protein contains repeating units.

It will be understood by those having skill in the art that the repeat sequence protein polymers of the present invention may be engineered to include appropriate repeating units in order to provide desired characteristics. For example, the repeat sequence protein polymers may be produced to have moisturizing properties, to have a high glass transition temperature for hardness or strength, and/or to have a high cloud temperature for heat sensitive applications. Similarly, the proteins may be produced to have a high isoelectric point to increase the affinity of the protein to hair, skin, and nails. The repeat sequence protein polymers may be engineered to provide or enhance or tailor the controlled release properties. For example, the molecular weight and composition of the protein may be chosen in order to increase or decrease water solubility, alter the diffusion coefficient, mechanical stength, biodegradability, or control the stimuli-sensitivity of the repeat sequence protein polymers as desired to enhance and tailor the controlled release properties of the repeat sequence protein polymer.

Polymers utilizing natural or synthetic repeating units may have their properties altered by appropriate choice of different units, the number of units in each multimer, the spacing between units, and the number of repeats of the multimer. Multimer refers to the portion of the polymer represented by $[(A_n)_x(B)_b(A'_{n'})_x(B')_b(A''_{n''})_{x''}]_i$ in the above formula. The spacing between units refers to the other amino acid sequences represented by B or B' in the above formula. Preferred copolymers are combinations of silk units and elastin units to provide silk-elastin copolymers having properties distinctive from polymers having only the same monomeric unit.

It will be understood by those having skill in the art that the repeat sequence protein polymers of the present invention may be produced to have a combination of desirable characteristics. For example a copolymer having silk repeating units and elastin repeating units may be produced to impart durability due to the silk repeating units and to impart flexibility due to the elastin repeating units. Additionally, the silk-elastin polymer may exhibit other desirable properties such as good clear film and hydrogel formation, which the individual monomeric units may not exhibit. The silk elastin copolymer may be water soluble. The silk elastin copolymer may undergo irreversible sol-to-gel transition. For example, by increasing the temperature to between about 37° C. to about 65° C. or by leaving the material at ambient temperature over time, the silk elastin copolymer may undergo either an irreversible or reversible sol-to-gel transition thereby forming water-insoluble films and hydrogels.

Water-insoluble films and hydrogels are desirable for controlled release of active ingredients in personal care products, particularly for products applied to the skin, because they reduce water loss from the skin and increase substantivity (remain on the skin). The silk elastin copolymer may also exhibit a high cloud temperature which is desirable in heat sensitive applications. The silk elastin copolymer may have a high isoelectric point which may make the copolymer more substantive to skin and hair. The silk elastin copolymer may further exhibit self assembly into fibers and films which may be desirable in some applications.

It will be further understood by those having skill in the art that the repeat sequence protein polymers of the present invention may be monodispersed or polydispersed. For purposes of defining and describing the present invention, "monodispersed" polymers are polymers having a single defined molecular weight. For purposes of defining and describing the present invention, "polydispersed" polymers are polymers that have been subjected to proteolysis and have a distribution of molecular weights.

Once a suitable repeat protein has been synthesized and purified, it may be used to form systems that may provide controlled release of active agents in any suitable personal care product formulation. For purposes of defining and describing the present invention, "active agent" shall be understood as referring to a suitable personal care product component including, but not limited to, enzymes; vitamins; anti-oxidants such as tocopherols ; moisturizing agents such as lactic acid, alpha hydroxy acids, Natural Moisturizing Factor (NMF); hyaluronic acid; fragrances; dyes; pigments; tints; UV filters; sunscreens; lanolin; bleaches; thickening agents; algae; plant extracts; and preservatives. For purposes of defining and describing the present invention, "controlled release" means release of at least one active agent from a system incorporating a repeat sequence protein polymer. By modifying the polymer properties and/or the design of the system, including type, geometry, and size, it is possible to obtain the required release rate over a specific period. Controlled release systems provide a fast, slow or constant release depending on the degree of control of both the optimum level and the optimum time of availability of the active ingredient. Controllable release mechanisms include, for example, diffusion through a rate controlling media, erosion of biodegradable barrier material, or a combination of diffusion and erosion. Controlled release further includes triggered release, which occurs in the presence of external conditions, such as heat, pressure, electric fields, pH, salt concentrations, ionic strength, and solvents.

In accordance with an embodiment of the present invention, a repeat sequence protein polymer and at least one active agent are used to form a complex, and the complex is further processed to provide a system capable of providing controlled release of an active agent. For purposes of defining and describing the present invention, "complex" means repeat sequence protein polymer and active agent associations wherein the repeat sequence protein polymer directly and passively interacts with moieties on the active agent molecules. The repeat sequence protein polymers may be amphiphilic having both hydrophilic and hydrophobic portions. The hydrophilic portion may interact with active molecules via hydrogen bonding, van der Waals interactions, and/or ionic interactions. Additionally, the hydrophobic portions may also interact with active agent molecules.

In accordance with an embodiment of the present invention, repeat sequence protein polymers may be used to form a complex with anionic molecules, and the complex may be further processed to provide a system, such as a matrix, gel, film or microparticle that may provide triggered controlled release of anionic molecules in personal care products. A suitable repeat sequence protein polymer may be used to form a complex with one or more anionic molecules. Generally, the repeat sequence protein polymer will be selected to be cationic, and the complex will be formed by an ionic interaction between the repeat sequence protein polymer and an active agent. Examples of suitable anionic molecules include, but are not limited to, anionic enzymes, such as glucose oxidase, lipases, and hydrolases, vitamin C, and alpha hydroxy acids such as glycolic acid, lactic acid, malic acid, citric acid, mixed fruit acid, triple fruit acid, and the like. The cationic repeat sequence protein polymer and anionic molecule complex may be formed in any suitable manner. For example, a repeat sequence protein polymer may be complexed with glucose oxidase by adding glucose oxidase to a repeat sequence protein polymer solution with or without additives, such as plasticizers (for instance, glycerol, PEG 200, triethanolamine, and the like).

Once a suitable complex has been formed, the complex is further processed to provide a system that is capable of providing controlled release of the active agents. For example, the temperature of the complex may be raised and the repeat sequence protein polymer may undergo an irreversible solto-gel transition to form a water-insoluble hydrogel or film to provide controlled release properties. In a further example, the complex may be left at ambient temperatures for a suitable period of time, and a water-insoluble hydrogel may be formed as the repeat sequence protein polymer undergoes an irreversible sol-to-gel transition. A water insoluble film may be formed by water evaporation Once a suitable system has been formed, the system may be used to provide controlled release of the anionic molecule. Generally, the anionic molecule may be released from the complex by changing the physical parameters of the environment of the complex. For example, the anionic molecule may be released by changing the ionic strength of the environment. When the ionic strength of the environment is increased, the charge-charge interaction of the complex may be affected, and the anionic molecule may be released.

In accordance with another embodiment of the present invention, repeat sequence protein polymers may form complexes having non-ionic interactions, and the complexes may form a material or carrier that may provide controlled release of active agents. For example, hydrophobic-hydrophobic, hydrogen bonding, and non-polar van der Waals type interactions may be utilized to form the complexes of the present invention. The active agent may be hydrophilic or hydrophobic. For example, the repeat sequence protein polymer and the active agents may exhibit a hydrophobic-hydrophobic interaction and/or hydrogen bonding and/or van der Waals type interactions, and a complex may be formed.

Once a suitable complex has been formed, the complex is further processed to provide a system that is capable of providing controlled release of the active agents. For example, the temperature of the complex may be raised and the repeat sequence protein polymer may undergo an irreversible sol-to-gel transition to form a water-insoluble hydrogel or film to provide controlled release properties. In a further example, the complex may be left at ambient temperatures for a suitable period of time, and a water-insoluble hydrogel may be formed as the repeat sequence protein polymer undergoes an irreversible sol-to-gel transition due to water evaporation. A water insoluble film may be formed by water evaporation.

The release of the active agent from the system may be due to diffusion through the repeat sequence protein polymer, erosion of the biodegradable repeat sequence protein polymer, shearing of the gel, hydrolyses of the protein polymer by protease present in the skin, or by any other suitable release mechanism. The repeat sequence protein polymer may act as a rate-controlling polymer. The release rate of the active agents from suitable repeat sequence protein polymers may be altered by modifying the composition and sequence of the repeat sequence protein polymer and by modifying the size and geometry of the repeat sequence protein polymer with which the active agent has been complexed. Examples of suitable hydrophilic active agents include but are not limited to enzymes, vitamin C, hyaluronic acid, and alpha hydroxy-acids. Examples of suitable hydrophobic active agents include, but are not limited to, vitamin E, vitamin D3, and coenzyme Q-10.

The repeat sequence protein polymer and active agent complex may be formed in any suitable manner. For example, enzyme aqueous solutions may be added to a repeat sequence protein polymer aqueous solution. The temperature of the mixture may then be raised to cause an irreversible sol-gel transition and form the water insoluble gel containing the enzyme. The enzyme repeat sequence polymer solution may also form an insoluble film by water evaporation. Vitamin E acetate may be emulsified into a repeat sequence protein polymer aqueous solution prior to forming gel or film as described above.

In an alternative embodiment, repeat sequence protein polymers may be complexed with suitable active agents, and the complexes may be used to form systems comprising microparticles that provide controlled release of active agents. The microparticles may be formed by an emulsion/gelation method using a suitable repeat sequence protein polymer which is caused to undergo irreversible sol-gel transition. When a water soluble active agent is used, the water soluble active agent and a suitable repeat sequence protein polymer may be added together in an aqueous solution so that a complex forms. The water soluble phase may then be emulsified into a second phase that is non-miscible to the aqueous phase. For example, the second phase may be an organic phase or a silicone phase. The emulsion may then be sheared until the desired droplet size is achieved, and the emulsion may be heated in order to increase the rate of gelation of the repeat sequence protein polymer. The technique results in small microparticles composed of repeat sequence protein polymer and an active agent embedded throughout the gel microparticles. The non-miscible phase may then be removed, and the microparticles may be added to suitable personal care product formulations.

When a water insoluble active is used, a two-step O/W/O emulsion/gelation process may be used. In the first step, the water insoluble active agent is emulsified into the repeat sequence protein polymer aqueous solution to form a complex. The emulsion is then added to another phase, or continuous phase, that is non-miscible to the aqueous phase and emulsified to form a O/W/O emulsion. The repeat sequence protein polymer is caused to undergo irreversible sol-gel transition by raising the temperature of the emulsion and the microparticles of repeat sequence protein polymer containing the water insoluble active agent are thus formed. The remaining continuous phase may be removed. The water soluble or water insoluble active agent may be released from the microparticles formed by the emulsion/gelation method by shearing because the microparticles are shear sensitive. Examples of suitable water soluble active agents include, but are not limited to, enzymes such as hydrolases, proteases, lipases, oxidases, peroxidases, amylases, carbohydrolases, and superoxide dismutases. Examples of suitable oil soluble active agents include, but are not limited to, Vitamins E and D3.

In accordance with another embodiment of the present invention, repeat sequence protein polymers are used to form microparticles from which the active agents may be released for use in personal care products. However, in this embodiment, a complex between the repeat sequence protein polymers and the active agents are generally not formed. The microparticles may be formed by interfacial polymerization reactions involving a repeat sequence protein polymer.

For example, the repeat sequence protein polymer may be water soluble and incorporated into a water soluble phase. An oil soluble monomer may be incorporated into an oil soluble phase. The water soluble phase and the oil soluble phase are added together to form an emulsion, and an interfacial polymerization reaction is carried out after the formation of the emulsion. The interfacial polymerization reaction may occur at the oil/water interface to form a capsule wall from the repeat sequence protein polymer and the monomer. A suitable water soluble active agent may be added to the water soluble phase prior to the formation of the emulsion. The water soluble phase having the repeat sequence protein polymer and the active agent may be added to the oil soluble phase having the oil soluble monomer to form an water/oil (W/O) emulsion prior to the interfacial polymerization reaction.

Alternatively, a suitable oil soluble active agent may be incorporated into the oil soluble phase containing a suitable oil soluble monomer. The oil soluble phase having the active agent may be added to the water soluble phase having a repeat sequence protein polymer to form an O/W emulsion prior to the interfacial polymerization reaction. The interfacial polymerization reaction may be carried out at room temperature or the reaction mixtures may be heated in order to speed the interfacial polymerization. Thus, the repeat sequence protein polymers may serve as encapsulating agents for both water soluble and water insoluble active agents.

Any suitable oil soluble monomer may be used to form the microparticles of the present invention. For example, suitable oil soluble monomers that may react with repeat sequence protein polymers include, but are not limited to, isocyanates, epoxides, alkylchlorides, and acid dichlorides. For example, an isocyanate monomer may react with an amine portion of a repeat sequence protein polymer. The active agent may be released from the microparticles in any suitable manner. For example, the active agent may be released by diffusion of the active out of the microparticle, shearing upon application of the microparticles to skin or hair that disrupts the capsule wall and releases the active agent, or hydrolyses of the protein polymer by protease present in the skin. For example, an oil soluble active agent may diffuse through the capsule wall upon application The size of the microparticles obtained by the emulsion/gelation or interfacial polymerization methods may be determined by the amount of shear employed when forming the emulsion. The microparticles containing the active agents may be added to any suitable personal care product. The microparticles of repeat sequence protein polymer may be soft and deformable to provide a desirable feel upon application on skin, hair, nails, etc. The repeat sequence protein polymer may be biodegradable, and its degradation product may generally be non-toxic. The microparticles of the present invention may allow the encapsulation and delivery of thermosensitive active agents such as enzymes as the encapsulation process using repeat sequence protein polymers generally involves mild temperatures. Additionally, the active agents may be protected from deactivation by the presence of water or other agents such as sodium stearate that may be present in personal care product formulations when the active agents are incorporated into the microparticles.

It will be understood that the systems incorporating repeat sequence protein polymer active agent complexes and systems having microparticles formed by interfacial polymerization of the present invention may have more than one active agent, and the active agents may be the same as or different from one another.

Additionally, the repeat sequence protein polymers of the present invention may be complexed with silicones, and the silicones will not generally be released from the complexes and microparticles of the present invention. Instead, the repeat sequence protein polymer silicone complexes may be used to provide delivery and release of other active agents.

Silicone, when incorporated into personal care compositions, is well-known in the art to confer benefits such as lubricity, conditioning and moisture retention, and to provide a desirable, non-greasy feel on skin. Typically, the silicone fluids are utilized in the form of aqueous emulsions for ease of incorporating them into skin or hair care formulations.

When incorporated into personal care compositions as a silicone-repeat sequence protein polymer complex, the silicone is believed to act in synergy with the repeat sequence protein polymer to enhance the personal care benefits provided by the protein polymer and any associated actives. In addition, the silicone acts to stabilize the repeat sequence protein polymer, increasing the protein solubility due to the resulting stable emulsion formation, which thereby increases the efficacy of the personal care compositions to which the complex has been added.

In one embodiment, the repeat sequence protein polymers are not only generally hydrophobic, but also water miscible, which distinguishes them from hydrolyzed forms. Proteins for which silicone provides delivery benefits include fibrous or structural proteins in general, and, in particular, silk-elastin like proteins (SELPs), collogen and keratin. A specific embodiment employs silicone to provide delivery benefits for the application of genetically engineered forms of these proteins, and, more specifically, genetically engineered forms of SELPs. An even more specific embodiment employs SELP47K (SEQ. ID. NO. 19).

In one embodiment, the silicone is combined with engineered forms of repeat sequence protein polymers in the form of emulsions, which improves the ease of delivery of these proteins into personal care products and, particularly, into personal care product compositions applied to skin or hair. Both silicone-continuous and aqueous-continuous emulsions are possible, though, personal care formulations are typically aqueous-based, and therefore silicone-repeat sequence protein polymer emulsions, wherein the continuous phase is aqueous, are desired for ease of delivery into such formulations. The repeat sequence protein polymers are interfacially active and adsorb at the silicone-water interface to stabilize the emulsions, either by themselves or in combination with surfactants. The use of silicone in combination with genetically engineered repeat sequence protein polymers allows formation of silicone emulsions with an aqueous continuous phase comprising up to about 95% by weight oil phase.

One silicone-based method embodiment for enhancing delivery of repeat sequence protein polymers utilizes silicone polyether (SPE) surfactants. SPEs are characterized as being amphiphilic, having a hydrophobic portion comprising the silicone, and hydrophilic polyether tails. Without being bound by theory, it is believed that the SPE interacts with the repeat sequence protein polymer to form a complex which helps dissolve the protein, resulting in an increase in the effective solubility of the protein. A more specific embodiment is directed to a method of utilizing silicone to enhance delivery of repeat sequence protein polymers wherein the repeat sequence protein polymer is a SELP. In a more specific embodiment, the SELP is SELP47K (SEQ. ID. NO. 19).

In another method embodiment utilizing silicone to enhance delivery of repeat sequence protein polymers, the repeat sequence protein polymer is added to emulsions of silicone in an aqueous continuous phase. It is believed that the hydrophobic portions of the repeat sequence protein polymers adsorb to the surface of the dispersed silicone fluid drops, while the hydrophilic portions interact with the aqueous phase. A specific embodiment utilizes SELPs as the repeat sequence protein polymer, and a more specific embodiment utilizes SELP47K as the repeat sequence protein polymer.

The stable silicone-repeat sequence protein polymer emulsions exhibit a high level of hysteresis, meaning that they are sensitive to the order of mixing. Preparation of emulsions with a continuous aqueous phase requires that the oil phase be added to the aqueous phase. In addition, the emulsions are sensitive to the method of mixing. Aqueous emulsions comprising a high percentage of the emulsion in the dispersed phase must be prepared by adding oil phase to water with mechanical agitation. The preferred surfactants, when employed, are silicone surfactants, in particular, silicone polyether polymeric surfactants. While the methods of preparation of these emulsions will be obvious to one of ordinary skill in the art, variations in the process by which the emulsions are prepared can result in silicone emulsions systems with different physical distributions of phases and of protein polymers, yielding a less effective emulsion delivery of the repeat sequence protein polymers.

These methods result in the formation of highly stable clear blue or creamy emulsions formed with simple mixing. Upon dilution, the repeat sequence protein polymer is maintained on the emulsion interface and the dispersed phase remains stable. In an embodiment directed to personal care compositions, the enhanced solubility of the protein and the silicone-repeat sequence protein polymer synergy with respect to personal care formulation benefits combine to comprise a product with unexpectedly high overall care benefits. In a specific personal care product embodiment, the stable silicone-repeat sequence protein polymer comprising the dispersed phase is incorporated in a personal care formulation directed to skin care, whereby the complex may be uniformly delivered to the skin via spreading.

The systems that may provide controlled release of active agents of the present invention may be added to rinse-off conditioners. The systems may be used in shampoos, gels, mousses, and other hair care products. The systems may be suitable for use in skin care products such as moisturizers, toners, and makeup. The systems may also be suitable for use in nail products such as polishes and polish remover.

The systems may be present in any suitable amount in product formulations. For example, the systems may comprise about from 0.001% to about 10% by weight of the composition. More generally, the systems may comprise about 0.01% to about 5% by weight of the composition, more preferably about 0.01% to about 1% by weight of the composition. In accordance with one embodiment of the present invention, the systems may be formulated into a variety of emulsions. The emulsions may provide moisturizing, softening, film formation, feel improvement, optical effects, strengthening, firming, and conditioning properties. The emulsions may contain:

| | |
|---|---|
| Water | qs |
| Emulsifier(s) | 1-5% |
| Thickener(s)/Stabilizer(s) | 0.1-3% |
| Emollient(s) | 2-10% |
| Opacifier(s) | 0-10% |
| Humectant(s) | 0-10% |
| Systems capable of providing controlled release | 0.001-10% |
| Functional ingredient(s) | 0.001-25% |
| Preservative | qs |
| Finishing ingredient(s) | qs |

It will be understood that the emulsions may additionally contain other suitable components. Suitable emulsifiers may be anionic, cationic, or nonionic in nature. For example, suitable emulsifiers include, but are not limited to, TEA stearate, ethoxylated fatty acids, or alcohols. Suitable thickeners may be any combination of ingredients used to modify product viscosity or rheology. The thickeners may be natural, and natural thickeners may include silicas, magnesium aluminum silicate, xanthan gum, and alginates. The thickeners may alternatively be polymeric, and polymeric thickeners may include acrylate crosspolymers, polyacrylic acid, and modified cellulosics. The thickeners may also include crystalline agents such as fatty acids and alcohols, and suitable crystalline agents include stearyl alcohol or stearic acid.

The emollients may be any combination of one or more ingredients used to modify product feel and aesthetics. Suitable emollients include: simple and complex esters such as isopropyl myristate and octyldodecyl stearoyl stearate; triglycerides such as capric/caprylic triglyceride; waxes such as carnauba and shea butter; vegetable or animal oils such as castor, coconut, and rice bran oil; fatty alcohols such as stearyl, myristyl, cetyl and behenyl alcohol; and fatty acids such as stearic, lauric and oleic acid.

Opacifiers may be any combination of one or more ingredients used to modify product appearance. Suitable opacifiers include, but are not limited to, fatty alcohols such as stearyl, myristyl, cetyl and behenyl alcohol and fatty acids such as stearic, lauric and oleic acid). Suitable humectants may be any combination of one or more ingredients used to retain moisture in the formula and impart hydration to the user. Suitable humectants include, but are not limited to, glycerin, propylene glycol, and sorbitol.

Functional ingredients may be any combination of one or more ingredients added to impart a specific effect when used and may be added to the personal care formulation in addition systems capable of providing controlled release of active agents. These can include: UV absorbers such as octyl methoxycinnamate, benzophenone-3, titanium dioxide, and octyl salicylate; film-forming agents such as VP/Eicosene copolymer; cosmeceutical agents such as peptides and proteins, alpha hydroxy acids, and retinol and retinoic acid derivatives; antioxidants such as tocopherol and derivatives thereof and ascorbic acid and derivatives thereof; vitamins such as B, D, K and their derivatives; antiperspirant actives such as aluminum hydroxide and zirconium hydroxide; depilating agents such as thioglycolate salts; anti-acne agents such as salicylic acid and benzoyl peroxide; abrasives and exfoliants such as silicates, pumice, and polyethylene; and extracts of plant, fruit, vegetable or marine sources.

Suitable preservatives may be any combination of ingredients approved by regulatory agencies and acceptable for use in cosmetic applications. For example, methyl and propyl paraben, imidazolidinyl urea, and sorbic acid may be used as perservatives. Finishing ingredients may be any combination of one or more ingredients added to adjust a formula's characteristics. Finishing ingredients may include: fragrance; colors; chelating agents such as tetrasodium EDTA; and pH buffers such as citric and phosphoric acid and salts.

Those skilled in the art may modify the illustrative emulsion formula for a variety of personal care applications. The emulsion formula may be used to form creams, lotions, moisturizers, facial cleansers, depilatories, masks, sun care products, antiperspirants, acne products, foundations, hair conditioners, hair relaxers, hair treatments, mascara, nail products, lip products, shaving products, and toothpaste, and the like.

In accordance with another embodiment of the present invention, the systems of the present invention may be formulated into a variety of surfactant systems. The surfactant systems may provide a number of properties to personal care products including moisturizing, softening, film formation, feel improvement, optical effects, strengthening, firming and conditioning. A typical surfactant systems may contain, but is not limited to, the following components:

| | |
|---|---|
| Water | qs |
| Primary surfactant(s) | 0.1-15% |

-continued

| | |
|---|---|
| Secondary surfactant(s) | 0.1-10% |
| Rheology modifier(s) | 0.1-5% |
| Alcohol(s) | 0-25% |
| Functional ingredient(s) | 0-10% |
| Conditioning ingredient(s) | 0-5% |
| Preservative(s) | qs |
| Finishing ingredient(s) | qs |
| Systems capable of providing controlled release | 0.001-10% |

It will be understood that additional, suitable components may be included in the surfactant systems. Primary surfactants may be any combination of one or more ingredients used to reduce surface tension or create foam. Surfactants may include; anionic surfactants such as alkyl sulfates, ether sulfates, alpha olefin sulfonates, and soap; amphoteric surfactants such as glucosides, glutamates, carboxylates, isethionates, carboxylates, glycinates, and lauramphoacetates; zwitterionic surfactants such as betaines and sultanes; or nonionic surfactants such as fatty alcohol ethoxylates, fatty acid ethoxylates, and amine oxides.

Secondary surfactants may be any combination of one or more ingredients used to modify foam characteristics and quality, stabilize foam, or reduce irritation. These can include, for example, cocoamidopropyl betaine, monoethanolamides, and diethanolamides. Suitable rheology modifiers can be any combination of one or more ingredients used to modify product appearance, viscosity or rheology. Rheology modifiers may be natural rheology modifiers, including salt, silicas, magnesium aluminum silicate, xanthan gum, guar derivatives, and alginates. Rheology modifiers may be polymeric rheology modifiers including acrylate crosspolymers, modified cellulosics, and polyacrylic acids. They may also include opacifiers and crystalline agents such as fatty acids and alcohols including stearyl alcohol or stearic acid. Suitable alcohols may be any combination of one or more ingredients added to provide astringency, cooling, volatility, or solubilization. For example, suitable alcohols include ethanol and isopropanol.

Functional ingredients may be any combination of one or more ingredients added to impart a specific effect when used. These can include: UV absorbers such as octyl methoxycinnamate and benzophenone-3; styling and film-forming agents such as polyvinyl pyrollidone (PVP) and PVP/polyvinyl alcohol (PVA) copolymers; cosmeceutical agents such as peptides, proteins, alpha hydroxy acids, retinal, and retinoic acid derivatives; antioxidants such as tocopherol and derivatives thereof and ascorbic acid and derivatives thereof; vitamins such as vitamins B, D, K and their derivatives; anti-acne agents such as salicylic acid and benzoyl peroxide; anti-dandruff agents such as zinc pyrithione and selenium sulfide; and conditioning agents such as cationic agents and extracts of plant, fruit, vegetable or marine sources.

Conditioning agents may be any combination of one or more ingredients added to impart moisturization, feel, smoothing, anti-static effects or shine. Suitable conditioning agents may include: cationic polymers such as polyquaternium-10 and polyquaternium-11; quaternized fatty acids such as cetyl trimethyl ammonium chloride; animal or vegetable proteins and their derivatives such as hydrolyzed wheat protein and hydrolyzed collagen; silicone derivatives such as dimethicones, amodimethicones, phenyl trimethicones, and volatile silicones; emollient oils such as isopropyl myristate and capric/caprylic triglyceride; and humectants such as glycerin and propylene glycol.

Those having skill in the art can modify this illustrative surfactant system formula for a variety of personal care applications. For example, the surfactant formula may be modified to form shampoos, body cleansers, facial cleansers, hair conditioners, hair gels, hair treatments, facial toners, fragrance products, and mouthwashes, and the like.

In accordance with an embodiment of the present invention a silk-elastin polymer SELP47K (SEQ ID NO. 19) may be used as the repeat sequence protein polymer of the present invention. The SELP47K is a homoblock protein polymer that consists exclusively of silk-like crystalline blocks and elastin-like flexible blocks. SELP47K is more linear than many proteins because it has a beta sheet two-dimensional structure rather than an alpha helix three-dimensional structure. SELP47K exhibits the ability to self-assemble by cross-linking of beta sheets into fibers. SELP47K is 70% proline, valine, and alanine, and has hydrophobic characteristics. Additionally, SELP47K has a high lysine ratio.

In order that the invention may be more readily understood, reference is made to the following examples, which are intended to be illustrative of the invention, but are not intended to be limiting in scope.

EXAMPLES

Example 1

A genetically engineered silk-elastin repeat sequence protein block copolymer (SELP) was isolated and purified from *E. coli* bacteria. The *E. coli* containing a specific silk-elastin repeat sequence protein copolymer SELP47K recombinant DNA was obtained from Protein Polymer Technologies, Inc. (PPTI) of San Diego, Calif. The *E. coli* may be prepared in accordance with the methods described in U.S. Pat. Nos. 5,243,038 and 6,355,776. The recovery of kilogram quantities of SELP was also demonstrated. The silk-elastin copolymer SELP47K had a general structure of head-[(GAGAGS)$_2$(GVGVP)$_3$GKGVP(GVGP)$_4$(GAGAGS)$_2$]$_{13}$-tail (SEQ ID NO. 19). The copolymer contained 886 amino acids, with 780 amino acids in the repeating sequence unit. The SELP47K had a molecular weight of about 70,000 Daltons, and the pI of the protein is 10.5.

Monodispersed silk-elastin protein polymer SELP47K was produced for application testing in the following manner. *E. coli* fermentation was performed to produce a cell-paste containing monodispersed SELP47K. The cell-paste was placed in ice cold water and homogenized to make the cell extract. The cell-extract was mixed with polyethyleneimine and a filter-aid and was allowed to stir at 7° C for one hour. The polyethyeleneimine caused precipitation of cell debris and a significant amount of *E. coli* proteins. The SELP47K containing reaction mixture was then filtered using Rotary Drum Vacuum Filter (RDVF). The filtered SELP47K solution was then mixed with ammonium sulfate to 25% saturation, which led to precipitation of SELP47K. Precipitated SELP47K and mother liquor was mixed with a filter-aid and again filtered using RDVF. The RDVF cake containing SELP47K and filter-aid was mixed with cold water to dissolve the SELP47K. This precipitation and solubilization step was repeated one more time to improve the purity profile of the SELP47K. Purified monodispersed SELP47K was then water-exchanged until the conductivity of SELP solution reached 50 µS/cm$^2$. The monodispersed SELP solution was then concentrated to 10% wt/vol and then lyophilized to make powdered monodispersed SELP47K protein polymer. The material was stored at −70° C. until needed for application testing.

B. SELP variants were either obtained from PPTI or genetically engineered (Table 1).

TABLE 1

SELP variants, properties.

| Variant Name | Number of Subunits | Lysine Substitution | Molecular Weight (Da) | Isoelectric Point |
|---|---|---|---|---|
| SELP47E | 13 | Glutamic Acid | 70,212 | 4.16 |
| SELP47K-3 | 3 | none | 20,748 | 9.52 |
| SELP47R-3 | 3 | Arginine | 20,960 | 10.5 |
| SELP47E-3 | 3 | Glutamic Acid | 20,879 | 5.9 |
| SELP27K | 13 | none | 59,401 | 10.53 |
| SELP37K | 13 | none | 64,605 | 10.53 |
| SELP58 | 13 | none | 74,765 | 6.7 |
| SELP67K | 13 | none | 80,347 | 10.53 |

The *E. coli* strains containing a specific silk-elastin repeat sequence protein copolymer SELP47K, SELP37K and SELP27K recombinant DNA were also obtained from Protein Polymer Technologies, Inc. of San Diego, Calif. SELP67K, SELP58, SELP37K and SELP27K variant proteins were produced in 14 L fed batch culture using standard SELP47K production protocols, as described above. Proteins were purified and characterized as follows: 40 grams of cell pastes collected from 14L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). SELP47K-3 species was excised from SDS-PAGE gels and further characterized, its identity confirmed, by LC-MS/MS (Liquid Chromatographic Mass Spectroscopy). The molecular weight of the intact SELP47K-3 protein was also confirmed using MALDI-TOF/MS (Matrix Assisted Laser Desorption Ionization Time of Flight Mass Spectrometry).

The protocol used for the genetic engineering of variants SELP47E, SELP47K-3, SELP47R-3, and SELP47E-3 is a modification of a commercially available kit designed to create single base pair changes in multiple sites along a particular DNA sequence (QUIKCHANGE® Multi (Site-Directed Mutagenesis Kit), Stratagene cat #200513). The standard protocol involves the construction of single direction 5' phosphorylated primers that will hybridize to plasmid template regions of interest and incorporate point mutations. Thermocycling is employed that includes a ligation reaction designed to link the multiple primers during each round of synthesis.

SELP DNA sequences are unique in that the multiple repeating subunits are identical. In order to change a single amino acid residue in all subunits a single change is effectively performed multiple times. The above protocol was further modified in that primers were designed pair-wise, complementary, thereby creating PCR amplification conditions in the thermocycling process. Amplified plasmid DNA was then used to transform *E. coli* cells and can be further screened and characterized for desired mutations.

Methods: Conversion of SELP lysine residues.

Primers were designed that direct a single base change mutation resulting in conversion of lysine residues to glutamic acids or arginines while simultaneously creating a unique restriction enzyme site at this location used for subsequent plasmid screening. 5' phosphorylated primers were made complementary, in both directions (both strands) as follows:

Glutamic Acid conversion:

5'-GGGAGTTGGTGTACCTGGAGAAGGTGTTCCG (SEQ ID NO. 21)
GGGGTAGG-3'

3'-CCCTCAACCACATGGACCTCTTCCACAAGGC (SEQ ID NO. 22)
CCCCATCC-5'

(A20 was converted to G20)
Arginine Conversion:

5'-GGGAGTTGGGGTACCTGGACGAGGTGTTCCG (SEQ ID NO. 23)
GGGGTAGG-3'

3'-CCCTCAACCCCATGGACCTCGAGGTGGAACC (SEQ ID NO. 24)
CCCCATCC-5'

(G19 and T20 were converted to C and G)

QUIKCHANGE® Multi reaction was carried out as per the manufacturer's protocol except that both complementary primers were included. 5 µl of each reaction was used to transform TOP10 cells as per protocol (Invitrogen). 100 µl of salt optimized carbon (SOC) outgrowth were plated per reaction. Transformants were picked and grown in 5 ml LB containing 50 ppm kanamycin. Plasmid DNA was obtained from cultures using the Qiagen plasmid miniprep kit and analyzed by digestion with appropriate restriction enzymes followed by gel electrophoresis. Constructs that appeared correct were confirmed by DNA sequencing. Several rounds of the above protocol were required to obtain the SELP47E variant. In all cases this method resulted in the creation of a library consisting of variants spanning a range of subunits. This distrubution ranged from 1 to 17 subunits. SELP47E-3 and SELP47R-3 were a result of this distribution. SELP47K-3 resulted from using the above methods to convert SELP47E-3 glutamic acids back to lysines.

Successful construct plasmids were used to transform *E. coli* MM294 using Lauryl Bertni (LB) plates containing 50 ppm kanamycin. Single colonies were picked and grown in 60 ml TM2 (recipe)+2% glucose, 50 ppm kanamycin in 500 ml fluted Erlemneyer flasks, 30° C., 250 rpm, 16 hrs. Cell culture was supplemented with glycerol (10% v/v), and 1.5 ml aliquots were placed in cryovials and stored at −80° C. Random vials were tested for contamination by incubating 10 µl inoculating loopfuls on LA+1.6% skim milk plates, 37° C., for 16 hrs. Integrity of the plasmids was also confirmed using plasmid purification and analysis using restriction enzyme digestion/gel electrophoresis as well as DNA sequencing. Frozen cryovials were prepared using methods known in the art and used as seed stocks for subsequent culturing, protein production.

SELP47K-3, SELP47E-3 and SELP47R-3 variant proteins were produced in 14 L fed batch culture using standard SELP47K production protocols used above. Proteins were purified and characterized as follows: 40 grams of cell pastes collected from 14L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). The SELP47K-3 species was excised from SDS-PAGE gels and further characterized, its identity confirmed, by LC-MS/MS. The molecular weight of the intact SELP47K-3 protein was also confirmed using MALDI-TOF/MS. −M3H+1641, M4H+1231 of silk-elastin unit. ~5 kDa Example 2

The purification and preparation of the polydispersed silk-elastin protein polymer for application testing was carried out in the following steps. A cell separation from the fermentation broth was done using microfiltration. A cell disruption to make a cell-extract was done using a French-press. The cell extract was separated from the cell-debris using polyethyleneimine and a filter-aid. The cell-extract was mixed with ammonium sulfate to 25% saturation to precipitate the silk-elastin protein polymer. The precipitated silk-elastin protein polymer was further purified by dissolving it in water and precipitating it with ammonium sulfate.

In order to prepare a polydispersed silk-elastin protein polymer, the precipitated silk-elastin protein polymer was again dissolved in water and mixed with a trace amount of commercial protease. The commercial protease was then inactivated and destroyed by acid treatment. The polydispersed silk-elastin protein polymer was then ultrafiltered until the silk-elastin protein polymer solution reached an electrical conductivity of 50 $\mu S/m^2$.

The polydispersed silk-elastin protein polymer solution was concentrated to 10 wt % and was lyophilized. The lyophilized polydispersed silk-elastin protein polymer powder was stored at −70° C. until use. The lyophilized polydispersed silk-elastin protein was then dissolved in deionized water to a desired concentration for hair application testing.

Example 3

The purification and formation of monomeric unit of SELP47K (4920 kDA molecular weight) was carried out using monodispersed material of SELP47K produced as in Example 1. The monodispersed SELP47K was dissolved in water and was treated with endopeptidase lysC protease (Sigma Chemical Company) specific for cleaving protein at lysine residue for 30 minutes at room temperature. The lysC protease was then inactivated and destroyed by acid treatment. The monomeric unit of SELP47K was then ultra-filtered until protein polymer solution conductivity reached 50 $\mu S/m^2$.

Example 4

A SELP47K and anionic glucose oxidase (Gox) film was formed in the following manner. A 12% SELP47K solution was prepared by adding 1.8 g of SELP47K to 13.2 g of milliQ water (pH 6.5). The solution was stirred with a magnetic bar for 15 mm. A Silverson mixer was used with a small head at 4000 rpm for 2 minutes until complete dissolution of SELP47K (no lumps) was obtained. A ~0.0647 g Gox stock solution and 0.06 g glycerol was added to 0.7 g of the ¯12% SELP47K solution, and the resulting mixture was stirred with a magnetic bar for 10 min at 300 rpm. The SELP47K/Gox mixture was dispensed onto a mylar sheet which was placed at 37° C. for 17 hours uncovered for the film to dry. The film was cooled to room temperature.

Example 5

A release rate study of Gox from a SELP47K and Gox film was conducted in the following manner. Portions of the film prepared in accordance with Example 3 were weighed accurately and mounted onto a 2.5 cm spherical glass piece using cement glue and allowed to dry for 30 minutes.

The release rate study of Gox from film was carried out using a Hanssen dissolution tester at 30° C. The glass mounted samples were placed into a narrow 150 ml dissolution vessel with the film facing up. 25 ml of buffer was added. One film sample had a milliQ water buffer. Another for film sample had a 0.2 M Na Phosphate pH 7.65 buffer. A small paddle that was placed just below the surface of the buffer and rotated at a speed of 25 rpm provided sample agitation. 0.5 ml samples were withdrawn at 10 min 20 min, 30 min, 1 hr, 2 hrs, 4 hr, 8 hr, 16 hr and 24 hr and were assayed for enzyme activity.

The Gox assay was conducted using a wave length of 410 nm at 25° C. and a reaction time of 10 minutes. A 50 $\mu l$ aliquot of sample was added to 1000 $\mu l$ of substrate solution (x21) and assayed for Gox activity. Gox concentration was calculated as follows: [Gox] (mg/ml)=(rate OD/min)*(0.6 $\mu g$/min) *(1 mg /1000 mg)*Dilution x21*Dilution*25. When the ionic 0.2 M Na Phosphate buffer is added to the film Gox is released in a controlled manner.

Example 6

A hydrogel incorporating a SELP47K and Gox polymer was prepared in the following manner. A 12% SELP47K solution was made by adding 2.4 g of SELP47K to 17.6 g of milliQ water (pH 6.5). The solution was stirred with a magnetic bar for 15 min. A Silverson mixer was used with a small head at 4000 rpm for 2 minutes until complete dissolution of SELP (no lumps) was obtained. 0.08 g of Gox stock solution was added to ~14.97 g of the 12% SELP solution and the resulting mixture was stirred with a magnetic bar for 10 min at 6000 rpm. ~3.0 g of the mixture was dispensed into a small plastic container (Rotronic) which was then closed and sealed with parafilm. The container was placed at 37° C. for 17 hours. After 17 hours, the hydrogel was cooled to room temperature.

Example 7

A release rate test of Gox from the hydrogel formed in accordance with Example 6 was conducted in the following manner. 1 ml milliQ water was added to wash the top surface of the hydrogel in the pastic container. The container was swirled twice and the wash was removed. The release rate in milliQ water was studied by adding 5 ml of milliQ water in the plastic container on top of the hydrogel. The container was closed and then swirled gently on a shaker at ~50 rpm. At various time points, 60 $\mu l$ samples of the dissolution medium were collected and assayed for Gox activity as described in Example 11. The release rate in 0.5M Na Phosphate buffer was studied by replacing the milliQ water 0.5M Sodium Phosphate buffer, pH 7.5 after 28 hours. The release rate assay as described above Example 11 was conducted.

The ionic 0.5 M Na Phosphate facilitated the release of Gox. Gox was stored for 17 hours at 37° C. and for 28 hours at room temperature. The initial activity of the Gox was observed. The Gox exhibited 66.59 mg/ml activity after 17 hours and 66.75 mg/ml activity after 28 hours. No degradation of the enzyme was observed.

Example 8

Microparticles formed around Gox using SELP47K may be prepared in the following manner. A 12 wt % aqueous solution of SELP47K is prepared by adding 2.4 g of SELP47K to 16.6 g of MilliQ water (pH 6.5). The mixture is then mixed using a Silverson mixer at 4000 rpm for 2 minutes until complete dissolution of SELP47K is obtained. 0.08 g of Glucose Oxidase (Gox) solution is added to 14.97 g of the 12% SELP47K aqueous solution and stirred with a magnetic bar for 10 minutes to obtain a homogeneous solution of Gox and SELP to form the water soluble phase. 2.25 g of a surfactant (Dow Corning 3225C) formulation aid is then blended with 30 g of silicone oil, 1000 Cts (Dow Corning) and added to a 50 ml beaker to form the oil soluble phase. A marine impeller is immersed to approximately half the liquid depth. SELP47K microparticles containing Gox are produced by an emulsion/gelation method. The SELP47K/Gox solution prepared above (15 g) is dispersed into the silicon oil and emulsified at 400 rpm for 15 minutes. The temperature of the emulsion is then brought up to 37° C. to initiate gelation of the emulsified SELP droplets and mixing is continued for 3 hours. The individual SELP47K microparticles containing Gox suspension in oil are thus obtained and may be blended into a personal care formulation.

The individual SELP47K microparticles containing Gox suspension in oil may also be added to a 200 ml beaker containing 100 ml milliQwater. The SELP47K microparticles settle into the lower aqueous phase, leaving the upper oil phase clear. The silicone oil is aspirated and discarded. The microparticles are then washed with 0.5% Tween 80 surfactant solution several times until the microspheres are free of oil. The SELP microparticle containing Gox suspended in milliQ water is then blended in a personal care formulation (water-based) such as O/W cream, lotions, shampoos, and the like.

Example 9

Microparticles formed around Gox using SELP47K may be prepared in the following manner. A 12 wt % aqueous solution of SELP47K is prepared by adding 2.4 g of SELP47K to 16.6 g of MilliQ water (pH 6.5). The mixture is mixed using a Silverson mixer at 4000 rpm for 2 minutes until complete dissolution of SELP47K is obtained. 0.08 g of Glucose Oxidase (Gox) solution may be added to 14.97 g of the 12% SELP47K aqueous solution and stirred with a magnetic bar for 10 minutes to obtain a homogeneous solution of Gox and SELP to form the water soluble phase. 30 ml jojoba oil blended with 2.25 g of Dow corning 5200 formulation aid is then added to a 50 ml beaker to form the oil soluble phase. A marin impeller is immersed to approximately half the liquid depth. SELP47K microparticles containing Gox are produced by an emulsion/gelation method. The SELP47K/Gox solution prepared above (15 g) is dispersed into the silicon oil and emulsified at 400 rpm for 15 minutes. The temperature of the emulsion is then brought up to 37° C. to initiate gelation of the emulsified SELP droplets and mixing is continued for 3 hours. The individual SELP47K microparticles containing Gox suspension in oil are thus obtained and are subsequently blended into a personal care formulation.

The individual SELP47K microparticles containing Gox suspension in oil can also be added to a 200 ml beaker containing 100 ml milliQwater. The SELP47K microparticles settle into the lower aqueous phase, leaving the upper oil phase clear. The jojoba oil is then aspirated and discarded. The microparticles are then washed with 0.5% tween 80 surfactant solution several times until the microspheres are free of oil. The SELP microparticle containing Gox suspended in milliQ water are then blended in a personal care formulation (water-based) such as O/W cream, lotions, shampoos, and the like.

Example 10

SELP47K microparticles containing Vitamin E surrounded by SELP47K may be prepared using the following method. An organic phase containing Vitamin E is prepared by mixing 15 g of Vitamin E, 15 g of the solvent Aromatic 100 and 2 g of Isocyanate monomer (polymethylene polyphenylisocyanate) to obtain a homogeneous phase.

An aqueous phase containing SELP47K may also be prepared. A 20 wt % aqueous solution of SELP is first made by adding 10 g of SELP to 40 g of MilliQ water (pH6.5). The mixture is then mixed using a Silverson mixer at 4000 rpm for 2 minutes until complete dissolution of SELP47K is obtained. Next, a surfactant is added to facilitate the emulsification of the organic phase. Specifically, 37.5 g of a 4% aqueous solution of Alcohol Ethoxylate Tergitol from Union Carbide is added to and mixed with 10 g of the 20 wt % SELP solution. A protective colloid is also added to enhance the emulsion stability. For instance, 5 g of a 10 wt % PVA aqueous solution (Mowiol 4-88 from Clariant Corporation) along with 15 g milliQ water is added. The aqueous phase is mixed to obtain a homogeneous phase before the addition of the organic phase and added to a 50 ml beaker. A marin impeller is immersed to approximately half the liquid depth.

The organic phase is then emulsified into the aqueous phase containing SELP47K. The previously prepared aqueous phase is stirred at 180 rpm while the organic phase is gradually introduced. Stirring of the mixture is then increased to 400 rpm for 15 minutes after all the organic phase is introduced. The emulsion is then transferred to a water bath and mild agitation at 250 rpm is then provided. The temperature of the emulsion is brought up to 37° C., to allow interfacial polymerization between SELP and the isocyanates monomers, and stirred at 37° C. for 3 hours.

Example 11

Delivery of SELP47K(SEQ. ID. NO.19) in a personal care formulation using silicone polyethers was performed as follows: silicone polyether DC193 (1.08 g) was taken in water (5.5% wt/wt) and blended with 6.75 g of 1000 centistocks (CS) polydimethylsiloxane 200 fluid. The mixture was allowed to stand for 30 minutes. To this mixture, solid SELP47K (1.08 g, 5.5% wt/wt, i.e. 1:1 Mass ratio to DC 193) was added. The mixture was then sheared until smooth (10 minutes) at 900 rpm using a stirrer. The resulting SELP47K-Silicone complex had an appearance of a bluish-tinge and was a stable emulsion. This emulsion, when analyzed by microscopy, revealed a fundamentally aqueous continuous phase with protein surrounding the discrete dispersed silicone phase.

What is claimed is:

1. A system for providing controlled release delivery of an active agent, comprising:

a repeat sequence protein polymer whose formula comprises $T_y[(A_n)_x(B)_b(A'_{n'})_{x'}(B')_{b'}(A''_{n''})_{x''}]_i T'_{y'}$, wherein: T and T' each comprise an amino acid or amino acid sequence of from about 1 to about 100 amino acids, wherein the amino acid or amino acid sequence of T is the same as or different from the amino acid or amino acid sequence of T'; y and y' are each an integer from 0 to 1, wherein the integer of y' is the same as or different from the integer of y;

A, A' and A" are each individual repeating sequence units comprising from about 3 to about 30 amino acids, wherein the amino acid sequence of A' and the amino acid sequence of A" are the same as or different from the amino acid sequence of A, and wherein A, A', and A" comprise at least one sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof;

n, n', and n" are integers of at least 2 and not more than 250;

x, x' and x" are each 0 or an integer of at least 1 with the proviso that not all of x, x', and x" can be 0, wherein each integer value for x, x', and x" varies to provide for at least 30 total amino acids in the A, A' and A" individual repeating sequence units, and wherein the integer of x' and the integer of x" are the same as or different from the integer of x;

B and B' each comprise an amino acid sequence of from about 4 to about 50 amino acids, wherein the amino sequence of B' is the same as or different from the amino acid sequence of B;

b and b' are each an integer from 0 to 3, wherein the integer of b' is the same as or different from the integer of b; and i is an integer from 1 to 100; and at least one active agent comprising a personal care product component selected from the group consisting of: enzymes, vitamins, anti-oxidants, moisturizing agents, alpha hydroxy acids, Natural Moisturizing Factor, hyaluronic acid, fragrances, dyes, pigments, tints, UV filters, sunscreens, lanolin, bleaches, thickening agents, algae, plant extracts, preservatives, and combinations thereof;

wherein the repeat sequence protein polymer and the at least one active agent form a complex wherein said repeat sequence protein polymer includes at least one hydrophilic or hydrophobic portion that interacts with said at least one active agent via hydrogen bonding, van der Waals interactions, non-ionic interactions, or ionic interactions.

2. The system as recited in claim 1, wherein T and T' comprise an amino acid or amino acid sequence from about 1 to about 60 amino acids.

3. The system as recited in claim 1, wherein T and T' comprise an amino acid or amino acid sequence with fewer than 20% of the total number of amino acids in the repeat sequence protein polymer.

4. The system as recited in claim 1, wherein B comprises an amino acid sequence with a biological or chemical activity.

5. The system as recited in claim 1, wherein B' comprises an amino acid sequence with a biological or chemical activity.

6. The system as recited in claim 1, wherein i is an integer from 1 to 50.

7. The system as recited in claim 1, wherein i is an integer from 1 to about 30.

8. The system as recited in claim 1, wherein A, A', and A" comprise at least one sequence selected from the group consisting of SEQ ID NO: 1, SEQ ID NO: 3, and combinations thereof.

9. The system as recited in claim 1, wherein the repeat sequence protein polymer comprises SEQ ID NO: 19.

10. The system as recited in claim 1, wherein the complex is formed by ionic interaction between the repeat sequence protein polymer and the at least one active agent and wherein the at least one active agent comprises anionic molecules and the repeat sequence protein polymer comprises cationic molecules.

11. The system as recited in claim 1 wherein the at least one active agent is selected from the group consisting of anionic enzymes and alpha-hydroxy acids.

12. The system as recited in claim 1 wherein the at least one active agent comprises an anionic enzyme selected from the group consisting of glucose oxidase, lipase, hydrolase, and combinations thereof.

13. The system as recited in claim 1 wherein the at least one active agent comprises glucose oxidase.

14. The system as recited in claim 1 wherein the complex is formed by non-ionic interaction between the repeat sequence protein polymer and the at least one active agent.

15. The system as recited in claim 14 wherein the non-ionic interaction between the repeat sequence protein polymer and the at least one active agent is hydrophobic.

16. The system of claim 1 wherein the system is formulated as a matrix, emulsion, gel, hydrogel, film or microparticles.

17. The system as recited in claim 16 wherein the controlled release delivery is a triggered release delivery.

18. A system for providing controlled release delivery of an active agent, comprising: a repeat sequence protein polymer whose formula comprises $T_y[(A_n)_x(B)_b(A'_{n'})_{x'}(B')_{b'}(A''_{n''})_{x''}]_i T'_{y'}$, wherein: T and T' each comprise an amino acid or amino acid sequence of from about 1 to about 100 amino acids, wherein the amino acid or amino acid sequence of T' is the same as or different from the amino acid or amino acid sequence of T; y and y' are each an integer from 0 to 1, wherein the integer of y' is the same as or different from the integer of y;

A, A' and A" are each individual repeating sequence units comprising from about 3 to about 30 amino acids, wherein the amino acid sequence of A' and the amino acid sequence of A" are the same as or different from the amino acid sequence of A, and wherein A, A', and A" comprise at least one sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof;

n, n', and n" are integers of at least 2 and not more than 250;

x, x' and x" are each 0 or an integer of at least 1 with the proviso that not all of x, x', and x" can be 0, wherein each integer value for x, x', and x" varies to provide for at least 30 total amino acids in the A, A' and A" individual repeating sequence units, and wherein the integer of x' and the integer of x" are the same as or different from the integer of x;

B and B' each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 100; and at least one active agent comprising a personal care product component selected from the group consisting of: enzymes, vitamins, anti-oxidants, moisturizing agents, alpha hydroxy acids, Natural Moisturizing Factor, hyaluronic acid, fragrances, dyes, pigments, tints, UV filters, sunscreens, lanolin, bleaches, thickening agents, algae, plant extracts, preservatives, and combinations thereof; and wherein the repeat sequence protein polymer and the at least one active agent form a complex of microparticles by an emulsion/gelation method.

19. The system as recited in claim 18 wherein the active agent is water soluble, and wherein the microparticles are formed by an emulsion/gelation method comprising: combining the water-soluble active agent and the repeat sequence protein polymer to form a complex in aqueous solution; emulsifying the complex as a water-soluble phase into a non-miscible phase so that the water-soluble phase forms dispersed phase droplets and the non-miscible phase forms a continuous phase; shearing the dispersed-phase droplets to a desired size; and removing the continuous phase.

20. The system as recited in claim 18 wherein the active agent is insoluble in water and wherein the repeat sequence protein polymer and the at least one water insoluble active agent form a complex of microparticles by an emulsion/gelation method comprising: emulsifying the water-insoluble active agent into an aqueous solution of the repeat sequence protein polymer to form an emulsion comprising a complex; emulsifying the emulsion as a water-soluble phase into a non-miscible phase so that the water-soluble phase forms dispersed-phase droplets and the non-miscible phase forms a continuous phase; shearing the dispersed-phase droplets to a desired size; and removing the continuous phase.

21. The system as recited in claim 18 wherein the microparticles comprise capsules formed by interfacial polymerization between the repeat sequence protein polymer and a suitable monomer, wherein the capsules comprise the at least one active agent encapsulated by the repeat sequence protein polymer formed by the interfacial polymerization.

22. The system as recited in claim 18 wherein the microparticles comprise more than one active agent, which may be the same or different.

23. A system for providing controlled release delivery of an active agent, comprising: a repeat sequence protein polymer whose formula comprises $T_y[(A_n)_x(B)_b(A'_{n'})_x(B')_b(A''_{n''})_{x''}]_i T'_{y'}$, wherein: T and T' each comprise an amino acid or amino acid sequence of from about 1 to about 100 amino acids, wherein the amino acid or amino acid sequence of T' is the same as or different from the amino acid or amino acid sequence of T; y and y' are each an integer from 0 to 1, wherein the integer of y' is the same as or different from the integer of y;

A, A' and A" are each individual repeating sequence units comprising from about 3 to about 30 amino acids, wherein the amino acid sequence of A' and the amino acid sequence of A" are the same as or different from the amino acid sequence of A, and wherein A, A', and A" comprise at least one sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof;

n, n', and n" are integers of at least 2 and not more than 250;

x, x' and x" are each 0 or an integer of at least 1 with the proviso that not all of x, x', and x" can be 0, wherein each integer value for x, x', and x" varies to provide for at least 30 total amino acids in the A, A' and A" individual repeating sequence units, and wherein the integer of x' and the integer of x" are the same as or different from the integer of x;

B and B' each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 100; and at least one active agent comprising a personal care product component selected from the group consisting of: enzymes, vitamins, anti-oxidants, moisturizing agents, alpha hydroxy acids, Natural Moisturizing Factor, hyaluronic acid, fragrances, dyes, pigments, tints, UV filters, sunscreens, lanolin, bleaches, thickening agents, algae, plant extracts, preservatives, and combinations thereof, wherein the repeat sequence protein polymer and the at least one active agent form a complex which is formulated into an emulsion comprising, by weight of the emulsion composition:

| | |
|---|---|
| water | qs |
| emulsifier(s) | 1-5% |
| thickener(s)/stabilizers | 0.1-3% |
| emollient(s) | 2-10% |
| opacifier(s) | 0-10% |
| humectant(s) | 0-10% |
| complex | 0.001-10% |
| functional ingredients | 0.001-25% |
| preservative(s) | qs |
| finishing ingredients | qs. |

24. A system for providing controlled release delivery of an active agent, comprising: a repeat sequence protein polymer whose formula comprises $T_y[(A_n)_x(B)_b(A'_{n'})_{x'}(B')_{b'}(A''_{n''})_{x''}]_i T'_{y'}$, wherein: T and T' each comprise an amino acid or amino acid sequence of from about 1 to about 100 amino acids, wherein the amino acid or amino acid sequence of T' is the same as or different from the amino acid or amino acid sequence of T; y and y' are each an integer from 0 to 1, wherein the integer of y' is the same as or different from the integer of y;

A, A' and A" are each individual repeating sequence units comprising from about 3 to about 30 amino acids, wherein the amino acid sequence of A' and the amino acid sequence of A" are the same as or different from the amino acid sequence of A, and wherein A, A', and A" comprise at least one sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof;

n, n', and n" are integers of at least 2 and not more than 250;

x, x' and x" are each 0 or an integer of at least 1 with the proviso that not all of x, x', and x" can be 0, wherein each integer value for x, x', and x" varies to provide for at least 30 total amino acids in the A, A' and A" individual repeating sequence units, and wherein the integer of x' and the integer of x" are the same as or different from the integer of x;

B and B' each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 100; and at least one active agent comprising a personal care product component selected from the group consisting of: enzymes, vitamins, anti-oxidants, moisturizing agents, alpha hydroxy acids, Natural Moisturizing Factor, hyaluronic acid, fragrances, dyes, pigments, tints, UV filters, sunscreens, lanolin, bleaches, thickening agents, algae, plant extracts, preservatives, and combinations thereof, wherein the repeat sequence protein polymer and the at least one active agent form a complex which is formulated into a surfactant system comprising, by weight of the surfactant system composition:

| | |
|---|---|
| water | qs |
| primary surfactant(s) | 0.1-15% |
| secondary surfactant(s) | 0.1-10% |
| rheology modifier(s) | 0.1-5% |
| alcohol(s) | 0-25% |
| complex | 0.001-10% |
| functional ingredient(s) | 0-10% |
| conditioning ingredient(s) | 0-5% |
| preservative(s) | qs |
| finishing ingredient(s) | qs. |

25. The system as recited in claim 17 wherein the triggered release delivery occurs in the presence of a change in heat, pressure, electric fields, pH, salt concentrations, ionic strength, solvents, or some combination thereof.

26. The system as recited in claim 17 wherein the triggered release delivery occurs in the presence of a change in ionic strength.

27. The system for providing controlled release delivery of an active agent according to claim 1, wherein the at least one active agent is anionic.

28. The system as recited in claim 1 wherein the repeat sequence protein polymer comprises SEQ ID NO:19 and wherein the at least one active agent comprises glucose oxidase.

29. The system as recited in claim 18 wherein the repeat sequence protein polymer comprises SEQ ID NO:19 and wherein the at least one active agent comprises glucose oxidase.

30. The system as recited in claim 23 wherein the repeat sequence protein polymer comprises SEQ ID NO:19 and wherein the at least one active agent comprises glucose oxidase.

31. The system as recited in claim 24 wherein the repeat sequence protein polymer comprises SEQ ID NO:19 and wherein the at least one active agent comprises glucose oxidase.

* * * * *

UNITED STATES PATENT AND TRADEMARK OFFICE
CERTIFICATE OF CORRECTION

PATENT NO. : 7,456,147 B2  Page 1 of 1
APPLICATION NO. : 10/845775
DATED : November 25, 2008
INVENTOR(S) : Manoj Kumar It is certified that error appears in the above-identified patent and that said Letters Patent is hereby corrected as shown below:

Col 2, Line 34, "polymer"0 (RSPP)" should read as -- polymer" (RSPP) --

Col 4, Line 60, "(Seq. ID NO. 17)" should read as -- (SEQ. ID NO. 17) --

Col 17, Line 59, "for 15mm" should read as -- for 15 min. --

Col 17, Line 62, "g of the -12%" should read as -- of the 12% --

Col 18, Line 16, "10 min 20 min, 30 min" should read as --10 min, 20 min, 30 min --

Signed and Sealed this

Twenty-first Day of April, 2009

JOHN DOLL
*Acting Director of the United States Patent and Trademark Office*

SEQUENCE LISTING

<160> NUMBER OF SEQ ID NOS: 31

<210> SEQ ID NO 1
<211> LENGTH: 6
<212> TYPE: PRT
<213> ORGANISM: unknown
<220> FEATURE:
<223> OTHER INFORMATION: silk fibroin peptide repeat sequence

<400> SEQUENCE: 1

Ser Gly Ala Gly Ala Gly
1               5

<210> SEQ ID NO 2
<211> LENGTH: 53
<212> TYPE: PRT
<213> ORGANISM: unknown
<220> FEATURE:
<223> OTHER INFORMATION: silk fibroin peptide repeat sequence

<400> SEQUENCE: 2

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Ala Gly Tyr
    50

<210> SEQ ID NO 3
<211> LENGTH: 5
<212> TYPE: PRT
<213> ORGANISM: unknown
<220> FEATURE:
<223> OTHER INFORMATION: elastin peptide sequence

<400> SEQUENCE: 3

Gly Val Gly Val Pro
1               5

<210> SEQ ID NO 4
<211> LENGTH: 10
<212> TYPE: PRT
<213> ORGANISM: unknown
<220> FEATURE:
<223> OTHER INFORMATION: artificial repeat sequence protein polymer
<220> FEATURE:
<221> NAME/KEY: misc_feature
<222> LOCATION: (10)..(10)
<223> OTHER INFORMATION: Xaa can be any naturally occurring amino acid

<400> SEQUENCE: 4

Gly Gly Phe Gly Gly Met Gly Gly Gly Xaa
1               5                   10

<210> SEQ ID NO 5
<211> LENGTH: 5
<212> TYPE: PRT
<213> ORGANISM: unknown
<220> FEATURE:
<223> OTHER INFORMATION: artificial repeat sequence protein polymer

<400> SEQUENCE: 5

```
Gly Pro Gly Gly Gly
1               5

<210> SEQ ID NO 6
<211> LENGTH: 6
<212> TYPE: PRT
<213> ORGANISM: unknown
<220> FEATURE:
<223> OTHER INFORMATION: artificial repeat sequence protein polymer

<400> SEQUENCE: 6

Pro Gly Gln Gly Gln Gln
1               5

<210> SEQ ID NO 7
<211> LENGTH: 9
<212> TYPE: PRT
<213> ORGANISM: unknown
<220> FEATURE:
<223> OTHER INFORMATION: artificial repeat sequence protein polymer

<400> SEQUENCE: 7

Gly Tyr Tyr Pro Thr Ser Pro Gln Gln
1               5

<210> SEQ ID NO 8
<211> LENGTH: 3
<212> TYPE: PRT
<213> ORGANISM: wheat

<400> SEQUENCE: 8

Gly Gln Gln
1

<210> SEQ ID NO 9
<211> LENGTH: 28
<212> TYPE: PRT
<213> ORGANISM: unknown
<220> FEATURE:
<223> OTHER INFORMATION: artificial repeat sequence protein polymer

<400> SEQUENCE: 9

Pro Pro Ala Lys Val Pro Glu Val Pro Lys Lys Pro Val Pro Glu Glu
1               5                   10                  15

Lys Val Pro Val Pro Val Pro Lys Lys Pro Glu Ala
            20                  25

<210> SEQ ID NO 10
<211> LENGTH: 12
<212> TYPE: PRT
<213> ORGANISM: human

<400> SEQUENCE: 10

Ser Pro Pro Pro Pro Ser Pro Lys Tyr Val Tyr Lys
1               5                   10

<210> SEQ ID NO 11
<211> LENGTH: 4
<212> TYPE: PRT
<213> ORGANISM: tomato

<400> SEQUENCE: 11

Arg Gly Asp Ser
1
```

```
<210> SEQ ID NO 12
<211> LENGTH: 5
<212> TYPE: PRT
<213> ORGANISM: unknown
<220> FEATURE:
<223> OTHER INFORMATION: artificial repeat sequence protein polymer

<400> SEQUENCE: 12

Pro Gln Gln Pro Tyr
1               5

<210> SEQ ID NO 13
<211> LENGTH: 5
<212> TYPE: PRT
<213> ORGANISM: unknown
<220> FEATURE:
<223> OTHER INFORMATION: artificial repeat sequence protein polymer

<400> SEQUENCE: 13

Pro Thr Thr Thr Lys
1               5

<210> SEQ ID NO 14
<211> LENGTH: 8
<212> TYPE: PRT
<213> ORGANISM: unknown
<220> FEATURE:
<223> OTHER INFORMATION: artificial repeat sequence protein polymer

<400> SEQUENCE: 14

Ala Gly Tyr Gly Ser Thr Gly Thr
1               5

<210> SEQ ID NO 15
<211> LENGTH: 8
<212> TYPE: PRT
<213> ORGANISM: unknown
<220> FEATURE:
<223> OTHER INFORMATION: artificial repeat sequence protein polymer

<400> SEQUENCE: 15

Tyr Gly Gly Ser Ser Gly Gly Gly
1               5

<210> SEQ ID NO 16
<211> LENGTH: 5
<212> TYPE: PRT
<213> ORGANISM: unknown
<220> FEATURE:
<223> OTHER INFORMATION: artificial repeat sequence protein polymer

<400> SEQUENCE: 16

Phe Gly Gly Gly Ser
1               5

<210> SEQ ID NO 17
<211> LENGTH: 6
<212> TYPE: PRT
<213> ORGANISM: unknown
<220> FEATURE:
<223> OTHER INFORMATION: artificial repeat sequence protein polymer

<400> SEQUENCE: 17

Thr Thr Thr Pro Asp Val
1               5

<210> SEQ ID NO 18
```

```
<211> LENGTH: 7
<212> TYPE: PRT
<213> ORGANISM: unknown
<220> FEATURE:
<223> OTHER INFORMATION: artificial repeat sequence protein polymer

<400> SEQUENCE: 18

Tyr Ser Pro Thr Ser Pro Ser
1               5

<210> SEQ ID NO 19
<211> LENGTH: 780
<212> TYPE: PRT
<213> ORGANISM: unknown
<220> FEATURE:
<223> OTHER INFORMATION: silk and elastin peptide repeats

<400> SEQUENCE: 19

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Lys Gly Val Pro
            20                  25                  30

Gly Val Gly Pro Gly Val Gly Pro Gly Val Gly Pro Gly Val Gly Pro
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Val Gly Val Pro Gly Val Gly
65                  70                  75                  80

Val Pro Gly Val Gly Val Pro Gly Lys Gly Val Pro Gly Val Gly Pro
                85                  90                  95

Gly Val Gly Pro Gly Val Gly Pro Gly Val Gly Pro Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Val Gly Val Pro Gly Val Gly Val Pro Gly Val
    130                 135                 140

Gly Val Pro Gly Lys Gly Val Pro Gly Val Gly Pro Gly Val Gly Pro
145                 150                 155                 160

Gly Val Gly Pro Gly Val Gly Pro Gly Ala Gly Ala Gly Ser Gly Ala
                165                 170                 175

Gly Ala Gly Ser Gly Ala Gly Ala Gly Ser Gly Ala Gly Ala Gly Ser
            180                 185                 190

Gly Val Gly Val Pro Gly Val Gly Val Pro Gly Val Gly Val Pro Gly
        195                 200                 205

Lys Gly Val Pro Gly Val Gly Pro Gly Val Gly Pro Gly Val Gly Pro
    210                 215                 220

Gly Val Gly Pro Gly Ala Gly Ala Gly Ser Gly Ala Gly Ala Gly Ser
225                 230                 235                 240

Gly Ala Gly Ala Gly Ser Gly Ala Gly Ala Gly Ser Gly Val Gly Val
                245                 250                 255

Pro Gly Val Gly Val Pro Gly Val Gly Val Pro Gly Lys Gly Val Pro
            260                 265                 270

Gly Val Gly Pro Gly Val Gly Pro Gly Val Gly Pro Gly Val Gly Pro
        275                 280                 285

Gly Ala Gly Ala Gly Ser Gly Ala Gly Ala Gly Ser Gly Ala Gly Ala
    290                 295                 300

Gly Ser Gly Ala Gly Ala Gly Ser Gly Val Gly Val Pro Gly Val Gly
```

-continued

```
            305                 310                 315                 320
Val Pro Gly Val Gly Val Pro Gly Lys Gly Val Pro Gly Val Gly Pro
                325                 330                 335
Gly Val Gly Pro Gly Val Gly Pro Gly Val Gly Pro Gly Ala Gly Ala
                340                 345                 350
Gly Ser Gly Ala Gly Ala Gly Ser Gly Ala Gly Ala Gly Ser Gly Ala
                355                 360                 365
Gly Ala Gly Ser Gly Val Gly Val Pro Gly Val Gly Val Pro Gly Val
            370                 375                 380
Gly Val Pro Gly Lys Gly Val Pro Gly Val Gly Pro Gly Val Gly Pro
385                 390                 395                 400
Gly Val Gly Pro Gly Val Gly Pro Gly Ala Gly Ala Gly Ser Gly Ala
                405                 410                 415
Gly Ala Gly Ser Gly Ala Gly Ala Gly Ser Gly Ala Gly Ala Gly Ser
                420                 425                 430
Gly Val Gly Val Pro Gly Val Gly Val Pro Gly Val Gly Val Pro Gly
            435                 440                 445
Lys Gly Val Pro Gly Val Gly Pro Gly Val Gly Pro Gly Val Gly Pro
        450                 455                 460
Gly Val Gly Pro Gly Ala Gly Ala Gly Ser Gly Ala Gly Ala Gly Ser
465                 470                 475                 480
Gly Ala Gly Ala Gly Ser Gly Ala Gly Ala Gly Ser Gly Val Gly Val
                485                 490                 495
Pro Gly Val Gly Val Pro Gly Val Gly Val Pro Gly Lys Gly Val Pro
            500                 505                 510
Gly Val Gly Pro Gly Val Gly Pro Gly Val Gly Pro Gly Val Gly Pro
            515                 520                 525
Gly Ala Gly Ala Gly Ser Gly Ala Gly Ala Gly Ser Gly Ala Gly Ala
            530                 535                 540
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
                565                 570                 575
Gly Val Gly Pro Gly Val Gly Pro Gly Val Gly Pro Gly Ala Gly Ala
                580                 585                 590
Gly Ser Gly Ala Gly Ala Gly Ser Gly Ala Gly Ala Gly Ser Gly Ala
                595                 600                 605
Gly Ala Gly Ser Gly Val Gly Val Pro Gly Val Gly Val Pro Gly Val
            610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
                645                 650                 655
Gly Ala Gly Ser Gly Ala Gly Ala Gly Ser Gly Ala Gly Ala Gly Ser
                660                 665                 670
Gly Val Gly Val Pro Gly Val Gly Val Pro Gly Val Gly Val Pro Gly
            675                 680                 685
Lys Gly Val Pro Gly Val Gly Pro Gly Val Gly Pro Gly Val Gly Pro
        690                 695                 700
Gly Val Gly Pro Gly Ala Gly Ala Gly Ser Gly Ala Gly Ala Gly Ser
705                 710                 715                 720
Gly Ala Gly Ala Gly Ser Gly Ala Gly Ala Gly Ser Gly Val Gly Val
                725                 730                 735
```

```
Pro Gly Val Gly Val Pro Gly Val Gly Val Pro Gly Lys Gly Val Pro
            740                 745                 750

Gly Val Gly Pro Gly Val Gly Pro Gly Val Gly Pro Gly Val Gly Pro
        755                 760                 765

Gly Ala Gly Ala Gly Ser Gly Ala Gly Ala Gly Ser
    770                 775                 780

<210> SEQ ID NO 20
<211> LENGTH: 3
<212> TYPE: PRT
<213> ORGANISM: unknown
<220> FEATURE:
<223> OTHER INFORMATION: artificial repeat sequence protein polymer
<220> FEATURE:
<221> NAME/KEY: misc_feature
<222> LOCATION: (2)..(3)
<223> OTHER INFORMATION: Xaa can be any naturally occurring amino acid

<400> SEQUENCE: 20

Gly Xaa Xaa
1

<210> SEQ ID NO 21
<211> LENGTH: 39
<212> TYPE: PRT
<213> ORGANISM: unknown
<220> FEATURE:
<223> OTHER INFORMATION: artificial repeat seqence protein polymer

<400> SEQUENCE: 21

Gly Gly Gly Ala Gly Thr Thr Gly Gly Thr Gly Thr Ala Cys Cys Thr
1               5                   10                  15

Gly Gly Ala Gly Ala Ala Gly Gly Thr Gly Thr Cys Cys Gly Gly
            20                  25                  30

Gly Gly Gly Thr Ala Gly Gly
        35

<210> SEQ ID NO 22
<211> LENGTH: 39
<212> TYPE: PRT
<213> ORGANISM: unknown
<220> FEATURE:
<223> OTHER INFORMATION: glycine-rich peptide

<400> SEQUENCE: 22

Cys Cys Cys Thr Cys Ala Ala Cys Cys Ala Cys Ala Thr Gly Gly Ala
1               5                   10                  15

Cys Cys Thr Cys Thr Thr Cys Cys Ala Cys Ala Ala Gly Gly Cys Cys
            20                  25                  30

Cys Cys Cys Ala Thr Cys Cys
        35

<210> SEQ ID NO 23
<211> LENGTH: 39
<212> TYPE: PRT
<213> ORGANISM: unknown
<220> FEATURE:
<223> OTHER INFORMATION: metallothionin peptide segments

<400> SEQUENCE: 23

Gly Gly Gly Ala Gly Thr Thr Gly Gly Gly Gly Thr Ala Cys Cys Thr
1               5                   10                  15

Gly Gly Ala Cys Gly Ala Gly Gly Thr Gly Thr Thr Cys Cys Gly Gly
```

```
                    20                  25                  30

Gly Gly Gly Thr Ala Gly Gly
         35

<210> SEQ ID NO 24
<211> LENGTH: 39
<212> TYPE: PRT
<213> ORGANISM: unknown
<220> FEATURE:
<223> OTHER INFORMATION: artificial glycine-rich peptide repeat

<400> SEQUENCE: 24

Gly Gly Gly Ala Gly Thr Thr Gly Gly Gly Thr Ala Cys Cys Thr
1               5                  10                  15

Gly Gly Ala Cys Gly Ala Gly Thr Gly Thr Thr Cys Cys Gly Gly
         20                  25                  30

Gly Gly Gly Thr Ala Gly Gly
         35

<210> SEQ ID NO 25
<211> LENGTH: 884
<212> TYPE: PRT
<213> ORGANISM: unknown
<220> FEATURE:
<223> OTHER INFORMATION: artificial glycine-rich peptide repeat sequence

<400> SEQUENCE: 25

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
         35                  40                  45

Gly Val Gly Val Pro Gly Val Gly Val Pro Gly Val Gly Val Pro Gly
     50                  55                  60

Glu Gly Val Pro Gly Val Gly Val Pro Gly Val Gly Glu Pro Gly Val
65                  70                  75                  80

Gly Val Pro Gly Ala Gly Ala Gly Ser Gly Ala Gly Ala Gly Ser Gly
                 85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Glu Gly Val Pro Gly Val Gly Val Pro Gly Val Gly Glu Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Glu Gly Val Pro Gly Val Gly Val Pro Gly Val Gly Glu Pro Gly Val
        195                 200                 205

Gly Val Pro Gly Ala Gly Ala Gly Ser Gly Ala Gly Ala Gly Ser Gly
    210                 215                 220

Ala Gly Ala Gly Ser Gly Ala Gly Ala Gly Ser Gly Val Gly Val Pro
225                 230                 235                 240
```

```
Gly Val Gly Val Pro Gly Val Gly Val Pro Gly Val Gly Val Pro Gly
            245                 250                 255
Glu Gly Val Pro Gly Val Gly Val Pro Gly Val Gly Glu Pro Gly Val
            260                 265                 270
Gly Val Pro Gly Ala Gly Ala Gly Ser Gly Ala Gly Ala Gly Ser Gly
            275                 280                 285
Ala Gly Ala Gly Ser Gly Ala Gly Ala Gly Ser Gly Val Gly Val Pro
            290                 295                 300
Gly Val Gly Val Pro Gly Val Gly Val Pro Gly Val Gly Val Pro Gly
305                 310                 315                 320
Glu Gly Val Pro Gly Val Gly Val Pro Gly Val Gly Glu Pro Gly Val
            325                 330                 335
Gly Val Pro Gly Ala Gly Ala Gly Ser Gly Ala Gly Ala Gly Ser Gly
            340                 345                 350
Ala Gly Ala Gly Ser Gly Ala Gly Ala Gly Ser Gly Val Gly Val Pro
            355                 360                 365
Gly Val Gly Val Pro Gly Val Gly Val Pro Gly Val Gly Val Pro Gly
            370                 375                 380
Glu Gly Val Pro Gly Val Gly Val Pro Gly Val Gly Glu Pro Gly Val
385                 390                 395                 400
Gly Val Pro Gly Ala Gly Ala Gly Ser Gly Ala Gly Ala Gly Ser Gly
            405                 410                 415
Ala Gly Ala Gly Ser Gly Ala Gly Ala Gly Ser Gly Val Gly Val Pro
            420                 425                 430
Gly Val Gly Val Pro Gly Val Gly Val Pro Gly Val Gly Val Pro Gly
            435                 440                 445
Glu Gly Val Pro Gly Val Gly Val Pro Gly Val Gly Glu Pro Gly Val
            450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
            485                 490                 495
Gly Val Gly Val Pro Gly Val Gly Val Pro Gly Val Gly Val Pro Gly
            500                 505                 510
Glu Gly Val Pro Gly Val Gly Val Pro Gly Val Gly Glu Pro Gly Val
            515                 520                 525
Gly Val Pro Gly Ala Gly Ala Gly Ser Gly Ala Gly Ala Gly Ser Gly
            530                 535                 540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
            565                 570                 575
Glu Gly Val Pro Gly Val Gly Val Pro Gly Val Gly Glu Pro Gly Val
            580                 585                 590
Gly Val Pro Gly Ala Gly Ala Gly Ser Gly Ala Gly Ala Gly Ser Gly
            595                 600                 605
Ala Gly Ala Gly Ser Gly Ala Gly Ala Gly Ser Gly Val Gly Val Pro
            610                 615                 620
Gly Val Gly Val Pro Gly Val Gly Val Pro Gly Val Gly Val Pro Gly
625                 630                 635                 640
Glu Gly Val Pro Gly Val Gly Val Pro Gly Val Gly Glu Pro Gly Val
            645                 650                 655
Gly Val Pro Gly Ala Gly Ala Gly Ser Gly Ala Gly Ala Gly Ser Gly
```

```
                      660                 665                 670
Ala Gly Ala Gly Ser Gly Ala Gly Ala Gly Ser Gly Val Gly Val Pro
            675                 680                 685

Gly Val Gly Val Pro Gly Val Gly Val Pro Gly Val Gly Val Pro Gly
        690                 695                 700

Glu Gly Val Pro Gly Val Gly Val Pro Gly Val Gly Glu Pro Gly Val
705                 710                 715                 720

Gly Val Pro Gly Ala Gly Ala Gly Ser Gly Ala Gly Ala Gly Ser Gly
                725                 730                 735

Ala Gly Ala Gly Ser Gly Ala Gly Ala Gly Ser Gly Val Gly Val Pro
            740                 745                 750

Gly Val Gly Val Pro Gly Val Gly Val Pro Gly Val Gly Val Pro Gly
        755                 760                 765

Glu Gly Val Pro Gly Val Gly Val Pro Gly Val Gly Glu Pro Gly Val
            770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
            805                 810                 815

Gly Val Gly Val Pro Gly Val Gly Val Pro Gly Val Gly Val Pro Gly
            820                 825                 830

Glu Gly Val Pro Gly Val Gly Val Pro Gly Val Gly Glu Pro Gly Val
        835                 840                 845

Gly Val Pro Gly Ala Gly Ala Gly Ser Gly Ala Gly Ala Gly Ser Gly
        850                 855                 860

Ala Gly Ala Met Asp Pro Gly Arg Tyr Gln Asp Leu Arg Ser His His
865                 870                 875                 880

His His His His

<210> SEQ ID NO 26
<211> LENGTH: 246
<212> TYPE: PRT
<213> ORGANISM: unknown
<220> FEATURE:
<223> OTHER INFORMATION: silk and elastin peptide repeat sequence

<400> SEQUENCE: 26

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Arg Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
            85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Arg Gly Val Pro Gly Val Gly Val Pro Gly Val Gly Val Pro
        130                 135                 140
```

```
Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Arg Gly Val Pro Gly Val Gly Val Pro Gly Val Gly Val Pro
            195                 200                 205

Gly Val Gly Val Pro Gly Ala Gly Ala Gly Ser Gly Ala Gly Ala Gly
        210                 215                 220

Ser Gly Ala Gly Ala Met Asp Pro Gly Arg Tyr Gln Asp Leu Arg Ser
225                 230                 235                 240

His His His His His
                245

<210> SEQ ID NO 27
<211> LENGTH: 244
<212> TYPE: PRT
<213> ORGANISM: unknown
<220> FEATURE:
<223> OTHER INFORMATION: silk and elastin peptide repeat sequence

<400> SEQUENCE: 27

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
        195                 200                 205

Gly Val Pro Gly Ala Gly Ala Gly Ser Gly Ala Gly Ala Gly Ser Gly
    210                 215                 220

Ala Gly Ala Met Asp Pro Gly Arg Tyr Gln Asp Leu Arg Ser His His
225                 230                 235                 240

His His His His
```

<210> SEQ ID NO 28
<211> LENGTH: 246
<212> TYPE: PRT
<213> ORGANISM: unknown
<220> FEATURE:
<223> OTHER INFORMATION: silk and elastin peptide repeat sequence

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Glu Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Glu Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220

Ser Gly Ala Gly Ala Met Asp Pro Gly Arg Tyr Gln Asp Leu Arg Ser
225                 230                 235                 240

His His His His His His
            245

<210> SEQ ID NO 29
<211> LENGTH: 1063
<212> TYPE: PRT
<213> ORGANISM: unknown
<220> FEATURE:
<223> OTHER INFORMATION: silk and elastin peptide repeat sequence

<400> SEQUENCE: 29

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala His Gly Pro Ala Gly Pro Lys Gly Ala His Gly Pro Ala
        35                  40                  45

Gly Pro Lys Gly Ala Gln Gly Pro Ala Gly Pro Gly Gly Ala Gln Gly
    50                  55                  60

-continued

```
Pro Ala Gly Pro Gly Gly Ala Gln Gly Pro Ala Gly Pro Gly Gly Ala
 65                  70                  75                  80
Gln Gly Pro Ala Gly Pro Gly Gly Ala Gln Gly Pro Ala Gly Pro Gly
                 85                  90                  95
Gly Ala Gln Gly Pro Ala Gly Pro Gly Gly Ala Gln Gly Pro Ala Gly
            100                 105                 110
Pro Gly Gly Ala Gln Gly Pro Ala Gly Pro Gly Gly Ala Gln Gly Pro
        115                 120                 125
Ala Gly Pro Gly Gly Ala Gln Gly Pro Ala Gly Pro Gly Gly Ala Gln
130                 135                 140
Gly Pro Ala Gly Pro Gly Gly Ala Gln Gly Pro Ala Gly Pro Gly Gly
145                 150                 155                 160
Ala Gln Gly Pro Ala Gly Pro Gly Gly Ala Gln Gly Pro Ala Gly Pro
                165                 170                 175
Gly Gly Ala Gln Gly Pro Ala Gly Pro Gly Gly Ala Gln Gly Pro Ala
            180                 185                 190
Gly Pro Gly Gly Ala Gln Gly Pro Ala Gly Pro Gly Gly Ala Gln Gly
        195                 200                 205
Pro Ala Gly Pro Gly Gly Ala Gln Gly Pro Ala Gly Pro Gly Gly Ala
210                 215                 220
Gln Gly Pro Ala Gly Pro Gly Gly Ala Gln Gly Pro Ala Gly Pro Gly
225                 230                 235                 240
Gly Ala Gln Gly Pro Ala Gly Pro Gly Gly Ala Gln Gly Pro Ala Gly
                245                 250                 255
Pro Gly Gly Ala Gln Gly Pro Ala Gly Pro Gly Gly Ala His Gly Pro
            260                 265                 270
Ala Gly Pro Lys Gly Ala His Gly Pro Ala Gly Pro Lys Gly Ala His
        275                 280                 285
Gly Pro Ala Gly Pro Lys Gly Ala His Gly Pro Ala Gly Pro Lys Gly
290                 295                 300
Ala Gln Gly Pro Ala Gly Pro Gly Gly Ala Gln Gly Pro Ala Gly Pro
305                 310                 315                 320
Gly Gly Ala Gln Gly Pro Ala Gly Pro Gly Gly Ala Gln Gly Pro Ala
                325                 330                 335
Gly Pro Gly Gly Ala Gln Gly Pro Ala Gly Pro Gly Gly Ala Gln Gly
            340                 345                 350
Pro Ala Gly Pro Gly Gly Ala Gln Gly Pro Ala Gly Pro Gly Gly Ala
        355                 360                 365
Gln Gly Pro Ala Gly Pro Gly Gly Ala Gln Gly Pro Ala Gly Pro Gly
370                 375                 380
Gly Ala Gln Gly Pro Ala Gly Pro Gly Gly Ala Gln Gly Pro Ala Gly
385                 390                 395                 400
Pro Gly Gly Ala Gln Gly Pro Ala Gly Pro Gly Gly Ala Gln Gly Pro
                405                 410                 415
Ala Gly Pro Gly Gly Ala Gln Gly Pro Ala Gly Pro Gly Gly Ala Gln
            420                 425                 430
Gly Pro Ala Gly Pro Gly Gly Ala Gln Gly Pro Ala Gly Pro Gly Gly
        435                 440                 445
Ala Gln Gly Pro Ala Gly Pro Gly Gly Ala Gln Gly Pro Ala Gly Pro
450                 455                 460
Gly Gly Ala Gln Gly Pro Ala Gly Pro Gly Gly Ala Gln Gly Pro Ala
465                 470                 475                 480
```

-continued

```
Gly Pro Gly Gly Ala Gln Gly Pro Ala Gly Pro Gly Gly Ala Gln Gly
            485                 490                 495
Pro Ala Gly Pro Gly Gly Ala Gln Gly Pro Ala Gly Pro Gly Gly Ala
        500                 505                 510
Gln Gly Pro Ala Gly Pro Gly Gly Ala His Gly Pro Ala Gly Pro Lys
    515                 520                 525
Gly Ala His Gly Pro Ala Gly Pro Lys Gly Ala His Gly Pro Ala Gly
530                 535                 540
Pro Lys Gly Ala His Gly Pro Ala Gly Pro Lys Gly Ala Gln Gly Pro
545                 550                 555                 560
Ala Gly Pro Gly Gly Ala Gln Gly Pro Ala Gly Pro Gly Gly Ala Gln
            565                 570                 575
Gly Pro Ala Gly Pro Gly Gly Ala Gln Gly Pro Ala Gly Pro Gly Gly
        580                 585                 590
Ala Gln Gly Pro Ala Gly Pro Gly Gly Ala Gln Gly Pro Ala Gly Pro
    595                 600                 605
Gly Gly Ala Gln Gly Pro Ala Gly Pro Gly Gly Ala Gln Gly Pro Ala
    610                 615                 620
Gly Pro Gly Gly Ala Gln Gly Pro Ala Gly Pro Gly Gly Ala Gln Gly
625                 630                 635                 640
Pro Ala Gly Pro Gly Gly Ala Gln Gly Pro Ala Gly Pro Gly Gly Ala
            645                 650                 655
Gln Gly Pro Ala Gly Pro Gly Gly Ala Gln Gly Pro Ala Gly Pro Gly
        660                 665                 670
Gly Ala Gln Gly Pro Ala Gly Pro Gly Gly Ala Gln Gly Pro Ala Gly
    675                 680                 685
Pro Gly Gly Ala Gln Gly Pro Ala Gly Pro Gly Gly Ala Gln Gly Pro
    690                 695                 700
Ala Gly Pro Gly Gly Ala Gln Gly Pro Ala Gly Pro Gly Gly Ala Gln
705                 710                 715                 720
Gly Pro Ala Gly Pro Gly Gly Ala Gln Gly Pro Ala Gly Pro Gly Gly
            725                 730                 735
Ala Gln Gly Pro Ala Gly Pro Gly Gly Ala Gln Gly Pro Ala Gly Pro
        740                 745                 750
Gly Gly Ala Gln Gly Pro Ala Gly Pro Gly Gly Ala Gln Gly Pro Ala
    755                 760                 765
Gly Pro Gly Gly Ala His Gly Pro Ala Gly Pro Lys Gly Ala His Gly
    770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
            805                 810                 815
Gly Ala Gln Gly Pro Ala Gly Pro Gly Gly Ala Gln Gly Pro Ala Gly
        820                 825                 830
Pro Gly Gly Ala Gln Gly Pro Ala Gly Pro Gly Gly Ala Gln Gly Pro
    835                 840                 845
Ala Gly Pro Gly Gly Ala Gln Gly Pro Ala Gly Pro Gly Gly Ala Gln
    850                 855                 860
Gly Pro Ala Gly Pro Gly Gly Ala Gln Gly Pro Ala Gly Pro Gly Gly
865                 870                 875                 880
Ala Gln Gly Pro Ala Gly Pro Gly Gly Ala Gln Gly Pro Ala Gly Pro
            885                 890                 895
Gly Gly Ala Gln Gly Pro Ala Gly Pro Gly Gly Ala Gln Gly Pro Ala
```

-continued

```
                900             905             910
Gly Pro Gly Gly Ala Gln Gly Pro Ala Gly Pro Gly Gly Ala Gln Gly
            915                 920                 925

Pro Ala Gly Pro Gly Gly Ala Gln Gly Pro Ala Gly Pro Gly Gly Ala
        930                 935                 940

Gln Gly Pro Ala Gly Pro Gly Gly Ala Gln Gly Pro Ala Gly Pro Gly
945                 950                 955                 960

Gly Ala Gln Gly Pro Ala Gly Pro Gly Gly Ala Gln Gly Pro Ala Gly
                965                 970                 975

Pro Gly Gly Ala Gln Gly Pro Ala Gly Pro Gly Gly Ala Gln Gly Pro
            980                 985                 990

Ala Gly Pro Gly Gly Ala Gln Gly Pro Ala Gly Pro Gly Gly Ala Gln
        995                 1000                1005

Gly Pro Ala Gly Pro Gly Gly Ala Gln Gly Pro Ala Gly Pro Gly
    1010                1015                1020

Gly Ala His Gly Pro Ala Gly Pro Lys Gly Ala His Gly Pro Ala
    1025                1030                1035

Gly Pro Lys Met Asp Pro Gly Arg Tyr Gln Leu Ser Ala Gly Arg
    1040                1045                1050

Tyr His Tyr Gln Leu Val Trp Cys Gln Lys
    1055                1060
```

<210> SEQ ID NO 30
<211> LENGTH: 1038
<212> TYPE: PRT
<213> ORGANISM: unknown
<220> FEATURE:
<223> OTHER INFORMATION: artificial repeat sequence protein polymer

<400> SEQUENCE: 30

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65              70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Lys Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Ala Gly
                165                 170                 175

Ala Gly Ser Gly Ala Gly Ala Gly Ser Gly Val Gly Val Pro Gly Val
            180                 185                 190

Gly Val Pro Gly Val Gly Val Pro Gly Val Gly Val Pro Gly Lys Gly
```

-continued

```
                195                 200                 205
Val Pro Gly Val Gly Val Pro Gly Val Gly Val Pro Gly Val Gly Val
    210                 215                 220

Pro Gly Ala Gly Ala Gly Ser Gly Ala Gly Ala Gly Ser Gly Ala Gly
225                 230                 235                 240

Ala Gly Ser Gly Ala Gly Ala Gly Ser Gly Ala Gly Ala Gly Ser Gly
                245                 250                 255

Ala Gly Ala Gly Ser Gly Val Gly Val Pro Gly Val Gly Val Pro Gly
                260                 265                 270

Val Gly Val Pro Gly Val Gly Val Pro Gly Lys Gly Val Pro Gly Val
            275                 280                 285

Gly Val Pro Gly Val Gly Val Pro Gly Val Gly Val Pro Gly Ala Gly
            290                 295                 300

Ala Gly Ser Gly Ala Gly Ala Gly Ser Gly Ala Gly Ala Gly Ser Gly
305                 310                 315                 320

Ala Gly Ala Gly Ser Gly Ala Gly Ala Gly Ser Gly Ala Gly Ala Gly
                325                 330                 335

Ser Gly Val Gly Val Pro Gly Val Gly Val Pro Gly Val Gly Val Pro
            340                 345                 350

Gly Val Gly Val Pro Gly Lys Gly Val Pro Gly Val Gly Val Pro Gly
            355                 360                 365

Val Gly Val Pro Gly Val Gly Val Pro Gly Ala Gly Ala Gly Ser Gly
            370                 375                 380

Ala Gly Ala Gly Ser Gly Ala Gly Ala Gly Ser Gly Ala Gly Ala Gly
385                 390                 395                 400

Ser Gly Ala Gly Ala Gly Ser Gly Ala Gly Ala Gly Ser Gly Val Gly
                405                 410                 415

Val Pro Gly Val Gly Val Pro Gly Val Gly Val Pro Gly Val Gly Val
                420                 425                 430

Pro Gly Lys Gly Val Pro Gly Val Gly Val Pro Gly Val Gly Val Pro
            435                 440                 445

Gly Val Gly Val Pro Gly Ala Gly Ala Gly Ser Gly Ala Gly Ala Gly
            450                 455                 460

Ser Gly Ala Gly Ala Gly Ser Gly Ala Gly Ala Gly Ser Gly Ala Gly
465                 470                 475                 480

Ala Gly Ser Gly Ala Gly Ala Gly Ser Gly Val Gly Val Pro Gly Val
                485                 490                 495

Gly Val Pro Gly Val Gly Val Pro Gly Val Gly Val Pro Gly Lys Gly
            500                 505                 510

Val Pro Gly Val Gly Val Pro Gly Val Gly Val Pro Gly Val Gly Val
            515                 520                 525

Pro Gly Ala Gly Ala Gly Ser Gly Ala Gly Ala Gly Ser Gly Ala Gly
            530                 535                 540

Ala Gly Ser Gly Ala Gly Ala Gly Ser Gly Ala Gly Ala Gly Ser Gly
545                 550                 555                 560

Ala Gly Ala Gly Ser Gly Val Gly Val Pro Gly Val Gly Val Pro Gly
                565                 570                 575

Val Gly Val Pro Gly Val Gly Val Pro Gly Lys Gly Val Pro Gly Val
            580                 585                 590

Gly Val Pro Gly Val Gly Val Pro Gly Val Gly Val Pro Gly Ala Gly
            595                 600                 605

Ala Gly Ser Gly Ala Gly Ala Gly Ser Gly Ala Gly Ala Gly Ser Gly
            610                 615                 620
```

```
Ala Gly Ala Gly Ser Gly Ala Gly Ala Gly Ser Gly Ala Gly Ala Gly
625                 630                 635                 640
Ser Gly Val Gly Val Pro Gly Val Gly Val Pro Gly Val Gly Val Pro
                645                 650                 655
Gly Val Gly Val Pro Gly Lys Gly Val Pro Gly Val Gly Val Pro Gly
            660                 665                 670
Val Gly Val Pro Gly Val Gly Val Pro Gly Ala Gly Ala Gly Ser Gly
        675                 680                 685
Ala Gly Ala Gly Ser Gly Ala Gly Ala Gly Ser Gly Ala Gly Ala Gly
    690                 695                 700
Ser Gly Ala Gly Ser Gly Ala Gly Ala Gly Ser Gly Ala Gly Val Gly
705                 710                 715                 720
Val Pro Gly Val Gly Val Pro Gly Val Gly Val Pro Gly Val Gly Val
                725                 730                 735
Pro Gly Lys Gly Val Pro Gly Val Gly Val Pro Gly Val Gly Val Pro
            740                 745                 750
Gly Val Gly Val Pro Gly Ala Gly Ala Gly Ser Gly Ala Gly Ala Gly
        755                 760                 765
Ser Gly Ala Gly Ala Gly Ser Gly Ala Gly Ala Gly Ser Gly Ala Gly
    770                 775                 780
Ala Gly Ser Gly Ala Gly Ala Gly Ser Gly Val Gly Val Pro Gly Val
785                 790                 795                 800
Gly Val Pro Gly Val Gly Val Pro Gly Val Gly Val Pro Gly Lys Gly
                805                 810                 815
Val Pro Gly Val Gly Val Pro Gly Val Gly Val Pro Gly Val Gly Val
            820                 825                 830
Pro Gly Ala Gly Ala Gly Ser Gly Ala Gly Ala Gly Ser Gly Ala Gly
        835                 840                 845
Ala Gly Ser Gly Ala Gly Ala Gly Ser Gly Ala Gly Ala Gly Ser Gly
    850                 855                 860
Ala Gly Ala Gly Ser Gly Val Gly Val Pro Gly Val Gly Val Pro Gly
865                 870                 875                 880
Val Gly Val Pro Gly Val Gly Val Pro Gly Lys Gly Val Pro Gly Val
                885                 890                 895
Gly Val Pro Gly Val Gly Val Pro Gly Val Gly Val Pro Gly Ala Gly
            900                 905                 910
Ala Gly Ser Gly Ala Gly Ala Gly Ser Gly Ala Gly Ala Gly Ser Gly
    915                 920                 925
Ala Gly Ala Gly Ser Gly Ala Gly Ala Gly Ser Gly Ala Gly Ala Gly
    930                 935                 940
Ser Gly Val Gly Val Pro Gly Val Gly Val Pro Gly Val Gly Val Pro
945                 950                 955                 960
Gly Val Gly Val Pro Gly Lys Gly Val Pro Gly Val Gly Val Pro Gly
                965                 970                 975
Val Gly Val Pro Gly Val Gly Val Pro Gly Ala Gly Ala Gly Ser Gly
            980                 985                 990
Ala Gly Ala Gly Ser Gly Ala Gly  Ala Gly Ser Gly Ala  Gly Ala Gly
        995                 1000                1005
Ser Gly  Ala Gly Ala Gly Ser  Gly Ala Gly Ala Gly  Ser Met Asp
    1010                1015                1020
Pro Gly  Arg Tyr Gln Asp Leu  Arg Ser His His  His His His
    1025                1030                1035
```

<210> SEQ ID NO 31
<211> LENGTH: 965
<212> TYPE: PRT
<213> ORGANISM: unknown
<220> FEATURE:
<223> OTHER INFORMATION: silk and elastin peptides

<400> SEQUENCE: 31

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Ala Gly Ala Gly Ser Gly
 65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Val Gly Val Pro Gly Val Gly Val
               100                 105                 110

Pro Gly Val Gly Val Pro Gly Val Gly Val Pro Gly Val Gly Val Pro
           115                 120                 125

Gly Val Gly Val Pro Gly Val Gly Val Pro Gly Val Gly Val Pro Gly
       130                 135                 140

Ala Gly Ala Gly Ser Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
               165                 170                 175

Val Pro Gly Val Gly Val Pro Gly Val Gly Val Pro Gly Val Gly Val
           180                 185                 190

Pro Gly Val Gly Val Pro Gly Val Gly Val Pro Gly Val Gly Val Pro
       195                 200                 205

Gly Val Gly Val Pro Gly Ala Gly Ala Gly Ser Gly Ala Gly Ala Gly
   210                 215                 220

Ser Gly Ala Gly Ala Gly Ser Gly Ala Gly Ala Gly Ser Gly Ala Gly
225                 230                 235                 240

Ala Gly Ser Gly Val Gly Val Pro Gly Val Gly Val Pro Gly Val Gly
               245                 250                 255

Val Pro Gly Val Gly Val Pro Gly Val Gly Val Pro Gly Val Gly Val
           260                 265                 270

Pro Gly Val Gly Val Pro Gly Val Gly Val Pro Gly Ala Gly Ala Gly
       275                 280                 285

Ser Gly Ala Gly Ala Gly Ser Gly Ala Gly Ala Gly Ser Gly Ala Gly
   290                 295                 300

Ala Gly Ser Gly Ala Gly Ala Gly Ser Gly Val Gly Val Pro Gly Val
305                 310                 315                 320

Gly Val Pro Gly Val Gly Val Pro Gly Val Gly Val Pro Gly Val Gly
               325                 330                 335

Val Pro Gly Val Gly Val Pro Gly Val Gly Val Pro Gly Val Gly Val
           340                 345                 350

Pro Gly Ala Gly Ala Gly Ser Gly Ala Gly Ala Gly Ser Gly Ala Gly
       355                 360                 365
```

```
Ala Gly Ser Gly Ala Gly Ala Gly Ser Gly Ala Gly Ala Gly Ser Gly
        370                 375                 380

Val Gly Val Pro Gly Val Gly Val Pro Gly Val Gly Val Pro Gly Val
385                 390                 395                 400

Gly Val Pro Gly Val Gly Val Pro Gly Val Gly Val Pro Gly Val Gly
                405                 410                 415

Val Pro Gly Val Gly Val Pro Gly Ala Gly Ala Gly Ser Gly Ala Gly
            420                 425                 430

Ala Gly Ser Gly Ala Gly Ala Gly Ser Gly Ala Gly Ala Gly Ser Gly
        435                 440                 445

Ala Gly Ala Gly Ser Gly Val Gly Val Pro Gly Val Gly Val Pro Gly
        450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Ala Gly
                485                 490                 495

Ala Gly Ser Gly Ala Gly Ala Gly Ser Gly Ala Gly Ala Gly Ser Gly
        500                 505                 510

Ala Gly Ala Gly Ser Gly Ala Gly Ala Gly Ser Gly Val Gly Val Pro
        515                 520                 525

Gly Val Gly Val Pro Gly Val Gly Val Pro Gly Val Gly Val Pro Gly
        530                 535                 540

Val Gly Val Pro Gly Val Gly Val Pro Gly Val Gly Val Pro Gly Val
545                 550                 555                 560

Gly Val Pro Gly Ala Gly Ala Gly Ser Gly Ala Gly Ala Gly Ser Gly
                565                 570                 575

Ala Gly Ala Gly Ser Gly Ala Gly Ala Gly Ser Gly Ala Gly Ala Gly
        580                 585                 590

Ser Gly Val Gly Val Pro Gly Val Gly Val Pro Gly Val Gly Val Pro
        595                 600                 605

Gly Val Gly Val Pro Gly Val Gly Val Pro Gly Val Gly Val Pro Gly
        610                 615                 620

Val Gly Val Pro Gly Val Gly Val Pro Gly Ala Gly Ala Gly Ser Gly
625                 630                 635                 640

Ala Gly Ala Gly Ser Gly Ala Gly Ala Gly Ser Gly Ala Gly Ala Gly
                645                 650                 655

Ser Gly Ala Gly Ala Gly Ser Gly Val Gly Val Pro Gly Val Gly Val
            660                 665                 670

Pro Gly Val Gly Val Pro Gly Val Gly Val Pro Gly Val Gly Val Pro
        675                 680                 685

Gly Val Gly Val Pro Gly Val Gly Val Pro Gly Val Gly Val Pro Gly
        690                 695                 700

Ala Gly Ala Gly Ser Gly Ala Gly Ala Gly Ser Gly Ala Gly Ala Gly
705                 710                 715                 720

Ser Gly Ala Gly Ala Gly Ser Gly Ala Gly Ala Gly Ser Gly Val Gly
                725                 730                 735

Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
        755                 760                 765

Gly Val Gly Val Pro Gly Ala Gly Ala Gly Ser Gly Ala Gly Ala Gly
        770                 775                 780

Ser Gly Ala Gly Ala Gly Ser Gly Ala Gly Ala Gly Ser Gly Ala Gly
```

-continued

```
                785                 790                 795                 800
Ala Gly Ser Gly Val Gly Val Pro Gly Val Gly Val Pro Gly Val Gly
                    805                 810                 815
Val Pro Gly Val Gly Val Pro Gly Val Gly Val Pro Gly Val Gly Val
                820                 825                 830
Pro Gly Val Gly Val Pro Gly Val Gly Val Pro Gly Ala Gly Ala Gly
            835                 840                 845
Ser Gly Ala Gly Ala Gly Ser Gly Ala Gly Ala Gly Ser Gly Ala Gly
    850                 855                 860
Ala Gly Ser Gly Ala Gly Ala Gly Ser Gly Val Gly Val Pro Gly Val
865                 870                 875                 880
Gly Val Pro Gly Val Gly Val Pro Gly Val Gly Val Pro Gly Val Gly
                885                 890                 895
Val Pro Gly Val Gly Val Pro Gly Val Gly Val Pro Gly Val Gly Val
                900                 905                 910
Pro Gly Ala Gly Ala Gly Ser Gly Ala Gly Ala Gly Ser Gly Ala Gly
            915                 920                 925
Ala Gly Ser Gly Ala Gly Ala Gly Ser Gly Ala Gly Ala Gly Ser Met
    930                 935                 940
Asp Pro Gly Arg Tyr Gln Leu Ser Ala Gly Arg Tyr His Tyr Gln Leu
945                 950                 955                 960
Val Trp Cys Gln Lys
            965
```